US012644151B2

(12) United States Patent (10) Patent No.: US 12,644,151 B2
Will (45) Date of Patent: Jun. 2, 2026

(54) COMPOSITIONS, KITS, AND METHODS FOR PERFORMING RAPID POLYMERASE CHAIN REACTIONS

(71) Applicant: Siemens Healthcare Diagnostics Inc., Tarrytown, NY (US)

(72) Inventor: Stephen Will, Oakland, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 711 days.

(21) Appl. No.: 17/757,627

(22) PCT Filed: Jan. 5, 2021

(86) PCT No.: PCT/US2021/070001
§ 371 (c)(1),
(2) Date: Jun. 17, 2022

(87) PCT Pub. No.: WO2021/142482
PCT Pub. Date: Jul. 15, 2021

(65) Prior Publication Data
US 2023/0040046 A1 Feb. 9, 2023

Related U.S. Application Data

(60) Provisional application No. 62/968,259, filed on Jan. 31, 2020, provisional application No. 62/959,240, filed on Jan. 10, 2020.

(51) Int. Cl.
*C12Q 1/686* (2018.01)
*C12Q 1/6813* (2018.01)
*C12Q 1/6853* (2018.01)

(52) U.S. Cl.
CPC ........... *C12Q 1/686* (2013.01); *C12Q 1/6813* (2013.01); *C12Q 1/6853* (2013.01)

(58) Field of Classification Search
CPC .. C12Q 1/6813; C12Q 1/6848; C12Q 1/6853; C12Q 1/686; C12Q 2525/101
See application file for complete search history.

(56) References Cited

U.S. PATENT DOCUMENTS

| | | | |
|---|---|---|---|
| 5,314,809 A | 5/1994 | Erlich et al. |
| 6,887,664 B2 | 5/2005 | Chen et al. |
| 2010/0151455 A1 | 6/2010 | Kutyavin |
| 2010/0256062 A1 | 10/2010 | Howard et al. |
| 2016/0017392 A1 | 1/2016 | Arnold et al. |
| 2016/0289736 A1 | 10/2016 | Jones et al. |
| 2018/0179581 A1 | 6/2018 | Wittwer et al. |
| 2018/0371549 A1 | 12/2018 | Boyd |
| 2019/0002954 A1 | 1/2019 | Wittwer et al. |

FOREIGN PATENT DOCUMENTS

| | | |
|---|---|---|
| CN | 106687589 | 5/2017 |
| CN | 107250382 | 10/2017 |
| WO | WO-2014153260 A1 * | 9/2014 ............. C12P 19/34 |
| WO | 2016007914 | 1/2016 |
| WO | WO-2016134059 A1 * | 8/2016 .......... C12Q 1/6806 |
| WO | 2018/125835 | 7/2018 |

OTHER PUBLICATIONS

Torija et al., "Identification and quantification of acetic acid bacteria in wine and vinegar by TaqMan-MGB probes," Food Microbiology, vol. 27, pp. 257-265. (Year: 2010).*
Myrick et al., "Integrated Extreme Real-Time PCR and High-Speed Melting Analysis in 52 to 87 Seconds," Clinical Chemistry, vol. 65, No. 2, pp. 263-271. (Year: 2019).*
Chen et al., "Novel multiplex PCR assay using locked nucleic acid (LNA)-based universal primers for the simultaneous detection of five swine viruses," Journal of Virological Methods, vol. 228, pp. 60-66. (Year: 2016).*
Wang et al., High-throughput SNP genotyping by single-tube PCR with Tm-shift primers. Biotechniques. Dec. 2005; 39(6):885-93.
Farrar, J.S. and Wittwer, C.T., (2015), Extreme PCR: Efficient and Specific DNA Amplification in 15-60 Seconds. Clinical Chemistry, 61, 145-153.
Bustin SA. How to speed up the polymerase chain reaction. Biomol Detect Quantif, (2017), 12:10-14.
Scott O Sundberg and others, Microfluidic Genotyping by Rapid Serial PCR and High-Speed Melting Analysis, Clinical Chemistry, vol. 60, Issue 10, Oct. 1, 2014, pp. 1306-1313.
Shaocai Du et al:, "Study on the effect of stabilizer protection on PCR amplification of dU-DNA"; Institute of Hepatology , The People's Hospital of Peking University; 13(2); pp. 4-6, Jan. 31, 2003, English Abstract.
International Search Report for PCT/US2021/070001 dated Mar. 26, 2021.
Schoenbrunner et al. "Covalent modification of primers improves PCR amplification specificity and yield," Biology Methode & Protocols, 2017, p. 1-10.
You et al. "Design of LNA probes \hat improve mismatch discrimination," Nucleic Acids Research, vol. 34, No. 8, May 2, 2006 (May 2, 2006), pp. 1-11.
Barnes III et al. "C5-(1-propynyl)-2'-deoxy-pyrimidines enhance mismatch penalties of DNA: RNA duplex formation," Biochemistry, vol. 40, No. 42, Sep. 26, 2001 (Sep. 26, 2001), pp. 12738-12745.
Belousov et al. "Single nucleotide polymorphism genotyping by two colour melting curve analysis using the MGB Eclipse(TM) Probe System in challenging sequence environment," Human Genomics, vol. 1, No. 3, Mar. 2004, pp. 209-217.
Duvall Jacquelyn A et al: "Rapid multiplex DNA amplification on an inexpensive microdevice for human identification via short tandem repeat analysis"; Analytica Chimica Acta; Elsevier; Amsterdam, NL; vol. 980, May 15, 2017; pp. 41-49.

* cited by examiner

*Primary Examiner* — Young J Kim

(57) ABSTRACT

Compositions, kits, and methods for performing rapid polymerase chain reaction (PCR) to amplify a target nucleic acid in a biological sample are disclosed. The methods include the use of at least one hybridization stabilizer and/or the adjustment of the thermocycling profiles between initiation and propagation phases of the amplification process. Also disclosed are methods of detecting the target nucleic acid following amplification thereof, as well as reaction mixtures that may be utilized in said methods.

32 Claims, 20 Drawing Sheets

Specification includes a Sequence Listing.

1.  Conventional primers and probe with native HBV amplicon
2.  Addition of GC-rich tails to ends of primers increases the Tm of each primer by 9-11°C
3.  Detection of amplicon in which GC-rich tails have been incorporated on 5' ends thereof and using a BHQ+ probe

Extension Temp and Duration- STD vs. GC-Tail Primers

Extension Temp and Duration- STD vs. GC-Tail Primers

COMPOSITIONS, KITS, AND METHODS FOR PERFORMING RAPID POLYMERASE CHAIN REACTIONS

CROSS REFERENCE TO RELATED APPLICATIONS/INCORPORATION BY REFERENCE STATEMENT

This application claims benefit under 35 USC § 119(e) of provisional applications U.S. Ser. No. 62/959,240, filed Jan. 10, 2020; and U.S. Ser. No. 62/968,259, filed Jan. 31, 2020. The entire contents of the above-referenced patents/patent applications are hereby expressly incorporated herein by reference.

STATEMENT REGARDING FEDERALLY SPONSORED RESEARCH OR DEVELOPMENT

Not Applicable.

BACKGROUND

Polymerase chain reaction (PCR) testing is a universally-accepted and widely-practiced laboratory method for replicating or amplifying the concentration of nucleic acid (NA), such as DNA, in a test tube. Replication/amplification takes place in an aqueous solution containing a concentration of DNA molecules. Pre-determined amounts of the polymerase enzyme, oligonucleotide primers, and tri-phosphates of the four nucleic acids or substrates are then added to the aqueous solution, which is then subjected to two thermal steps, referred to as the denaturing step and the annealing/elongation step.

During the first, denaturing step, the DNA double helix in aqueous solution is heated at a high temperature (such as between about 90 and 95° C.) so that each strand of the double helix is separated from the other. During the second, annealing/elongation step, the denatured aqueous solution is cooled (such as to a temperature between about 60 and about 72° C.), causing the oligonucleotide primers to attach to complementary nucleotide sequences of each denatured DNA strand and reforming of the DNA double helices by elongation of the primers. More specifically, a thermostable polymerase, such as Taq-polymerase, bonds nucleotides to the primer attached to the complementary nucleotide sequences, which forms two new DNA double helices where before there was just one. Accordingly, with every complete cycle, there is a doubling of the number of DNA molecules, so that the number of DNA molecules after n cycles is equal to $N_0 \times 2^n$ (where $N_0$ is the initial copy number).

While theoretically each of these steps needs only 3-30 seconds to complete, in practice, however, the duration of each thermal step is affected by many different factors that increase the turnaround time (TAT) for the PCR reaction; these factors affect the rate of heat transfer to heat or cool the aqueous solution at the pre-determined thermal cycle temperature. Variables that can affect the heating/cooling rates include (for example, but not by way of limitation) the volume of the solution, the concentration of the aqueous solution, the thermal conductivity of the vessel holding the nucleic acid in aqueous solution, the thermal conductivity of the apparatus holding the vessel, and the method of applying and removing heat, e.g., by conduction or convection.

The conventional ramp rates, amplicon sizes, and oligo denaturation temperatures are not optimal for all the desired features of rapid and efficient PCR amplification. Other groups have disclosed certain adaptations of PCR reagents and PCR thermocycling profiles to facilitate faster PCR reactions (see, for example, US Patent Application Nos. US 2010/0256062; US 2016/0289736; US 2018/0179581; and US 2019/0002954; International Patent Publication No. WO 2018/125835; and Wang et al. (*Biotechniques* (2005) 39:885-893); Farrar et al. (*Clinical Chemistry* (2015) 61:145-153); Bustin (*Biomolecular Detection and Quantification* (2017) 12:10-14); and Sundberg et al. (*Clinical Chemistry* (2014) 60:1306-1313); however, the methods disclosed in the prior art do not provide the turnaround time and target specific signal generation (real time PCR) that would be required in order to commercialize assays of infectious diseases, for example.

Thus, there is a need in the art for new and improved PCR methods that implement very rapid thermocycling profiles and thus produce rapid turnaround times while maintaining the sensitivity and selectivity of the target specific signal generation that would render the methods adaptable to near patient testing using a Point of Care (POC) diagnostic device, particularly for time critical assays. It is to such new and improved PCR methods, as well as compositions, kits, and reaction mixtures utilized for same, that the present disclosure is directed.

DETAILED DESCRIPTION

Figure 1:
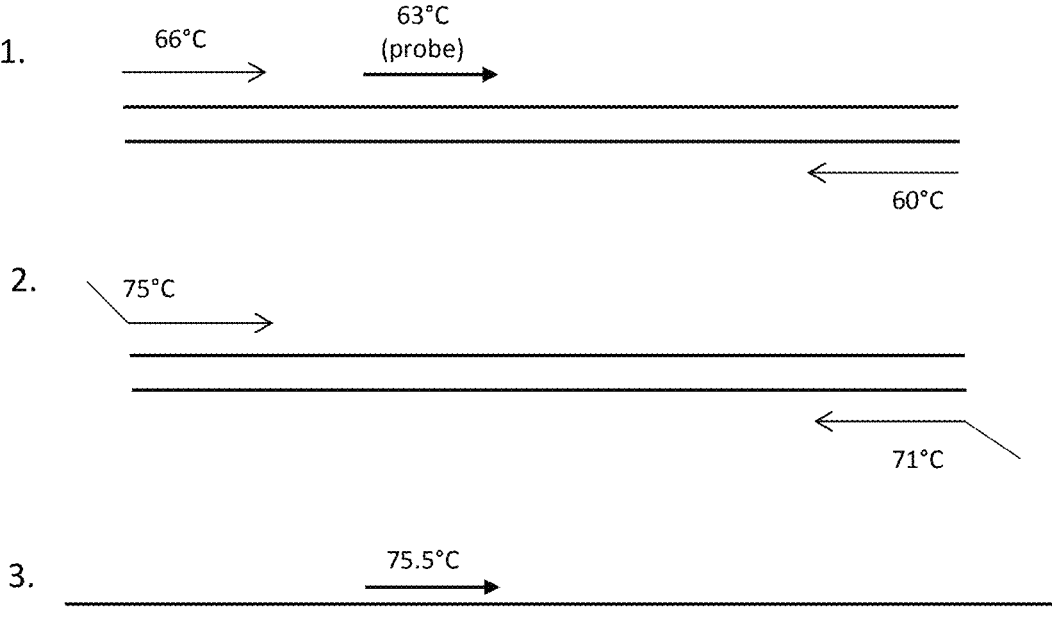
FIG. 1 schematically illustrates the construction of PCR primers and probes containing hybridization stabilizers in accordance with the present disclosure.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and termi- nology employed herein is for the purpose of description and should not be regarded as limiting.

Unless otherwise defined herein, scientific and technical terms used in connection with the presently disclosed inven- tive concept(s) shall have the meanings that are commonly understood by those of ordinary skill in the art. Further, unless otherwise required by context, singular terms shall include pluralities and plural terms shall include the singu- lar. The foregoing techniques and procedures are generally performed according to conventional methods well known in the art and as described in various general and more specific references that are cited and discussed throughout the present specification. The nomenclatures utilized in connection with, and the laboratory procedures and tech- niques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All pat- ents, published patent applications, and non-patent publica- tions referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be under- stood to have the following meanings:

The use of the term "a" or "an" when used in conjunction with the term "comprising" in the claims and/or the speci- fication may mean "one," but it is also consistent with the meaning of "one or more," "at least one," and "one or more than one." As such, the terms "a," "an," and "the" include plural referents unless the context clearly indicates other- wise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differen- tiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "com- prise" and "comprises"), "having" (and any form of having, such as "have" and "has"), "including" (and any form of including, such as "includes" and "include"), or "contain- ing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are com- binations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circum- stance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The terms "polynucleotide" and "nucleic acid" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component. The terms "isolated nucleic acid" and "isolated polynucleotide" are used interchangeably; a nucleic acid or polynucleotide is considered "isolated" if it: (1) is not associated with all or a portion of a polynucleotide in which the "isolated polynucleotide" is found in nature, (2) is linked to a polynucleotide to which it is not linked in nature, or (3) does not occur in nature as part of a larger sequence.

The term "naturally-occurring" as used herein as applied to an object refers to the fact that an object can be found in nature. For example, a polynucleotide or polypeptide sequence that is present in an organism (including viruses) that can be isolated from a source in nature and which has not been intentionally modified by man in the laboratory or otherwise is naturally-occurring. The term "naturally-occurring" may be used interchangeably herein with the term "native."

The term "selectively hybridize" referred to herein means to detectably and specifically bind. Polynucleotides, oligonucleotides and fragments thereof encoding peptides/polypeptides/proteins in accordance with the inventive concept (s) selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the inventive concept(s) and a nucleic acid sequence of interest will be at least 80%, and more typically with increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred (but non-limiting), with 2 or less being more preferred (but non-limiting). Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA."

The following terms are used to describe the sequence relationships between two or more polynucleotide or amino acid sequences: "reference sequence," "comparison window," "sequence identity," "percentage of sequence identity," and "substantial identity." A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window," as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Adv. Appl. Math., 2:482 (1981)), by the homology alignment algorithm of Needleman and Wunsch (J. Mol. Biol., 48:443 (1970)), by the search for similarity method of Pearson and Lipman (Proc. Natl. Acad. Sci. (U.S.A.), 85:2444 (1988)), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages, or by inspection, and the best alignment (i.e., resulting in the highest percentage of homology over the comparison window) generated by the various methods is selected.

The term "sequence identity" means that two polynucleotide or amino acid sequences is identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, such as at least 90 to 95 percent sequence identity, or at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

The terms "analog" or "variant" as used herein will be understood to refer to a variation of the normal or standard form or the wild-type form of molecules. For polypeptides or polynucleotides, an analog may be a variant (polymorphism), a mutant, and/or a naturally or artificially chemically modified version of the wild-type polynucleotide (including combinations of the above). Such analogs may have higher, full, intermediate, or lower activity than the normal form of the molecule, or no activity at all. Alternatively and/or in addition thereto, for a chemical, an analog may be any structure that has the desired functionalities (including alterations or substitutions in the core moiety), even if comprised of different atoms or isomeric arrangements.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

Turning now to the inventive concepts, very rapid PCR methods are disclosed that include the use of two unique features: the use of multiple thermocycling profiles that have been adjusted based on the amplicon produced, and the use of a hybridization stabilizer with the primers or probe. The very rapid PCR methods of the present disclosure provide a rapid turnaround times while maintaining the sensitivity and selectivity of the target specific signal generation; as such, the PCR methods disclosed herein are adaptable to near patient testing using a Point of Care (POC) diagnostic device, which will be particularly valuable for time critical assays.

Certain non-limiting embodiments of the present disclosure are directed to a method of amplifying a target nucleic acid in a biological sample. The method includes the steps of: (i) adding a thermostable polymerase, nucleotides, and a pair of primers configured for amplification of the target nucleic acid to the biological sample to create an amplification mixture, wherein at least one of the primers comprises a hybridization stabilizer; and (ii) amplifying the target nucleic acid by polymerase chain reaction by thermally cycling the amplification mixture between at least a denaturation temperature and an elongation temperature through a plurality of amplification cycles using a temperature cycling profile. In addition, the plurality of amplification cycles comprises at least one initiation cycle and at least one propagation cycle, and the thermocycling profile of the initiation cycle is different from the thermocycling profile of the propagation cycle.

In certain non-limiting embodiments, each of the initiation cycle(s) is completed in a cycle time of equal to or less than about 60 seconds per cycle, such as (but not limited to) equal to or less than about 55 seconds, equal to or less than about 50 seconds, equal to or less than about 45 seconds, equal to or less than about 40 seconds, equal to or less than about 35 seconds, equal to or less than about 30 seconds, equal to or less than about 25 seconds, equal to or less than about 20 seconds, equal to or less than about 19 seconds, equal to or less than about 18 seconds, equal to or less than about 17 seconds, etc. Also, each of the propagation cycle(s) is completed in a cycle time of equal to or less than about 30 seconds, such as (but not limited to) equal to or less than about 29 seconds, equal to or less than about 28 seconds, equal to or less than about 27 seconds, equal to or less than about 26 seconds, equal to or less than about 25 seconds, equal to or less than about 24 seconds, equal to or less than about 23 seconds, equal to or less than about 22 seconds, equal to or less than about 21 seconds, equal to or less than about 20 seconds, equal to or less than about 19 seconds, equal to or less than about 18 seconds, equal to or less than about 17 seconds, equal to or less than about 16 seconds, equal to or less than about 15 seconds, equal to or less than about 14 seconds, equal to or less than about 13 seconds, equal to or less than about 12 seconds, equal to or less than about 11 seconds, equal to or less than about 10 seconds, equal to or less than about 9 seconds, equal to or less than about 8 seconds, equal to or less than about 7 seconds, equal to or less than about 6 seconds, equal to or less than about 5 seconds, equal to or less than about 4 seconds, equal to or less than about 3 seconds, equal to or less than about 2 seconds, etc.

In certain non-limiting embodiments, the thermocycling profiles of the initiation and propagation cycles differ from one another in at least one parameter. For example (but not by way of limitation), the thermocycling profile of the propagation cycle may have a different denaturation temperature, denaturation duration/time, elongation temperature, elongation duration/time, ramp rate, and/or cycle completion time when compared to the thermocycling profile of the initiation cycle. The thermocycling profiles may differ in at least one of these parameters, at least two of these parameters, at least three of these parameters, at least four of these parameters, at least five of these parameters, or all six of these parameters.

The amplicon may possess any melt/denaturation temperature and any length so long as the amplicon can be produced by the methods disclosed herein. For example (but not by way of limitation), the amplicon may have a full denaturation temperature of about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or higher. In addition, the amplicon may have a full denaturation temperature that falls within a range formed of any of the above referenced values (such as, but not limited to, a range of from about 85° C. to about 95° C., a range of from about 85° C. to about 92° C., etc.). Non-limiting examples of amplicon length that may be utilized in accordance with the present disclosure include, but are not limited to, less than or equal to about 300 bp, less than or equal to about 290 bp, less than or equal to about 280 bp, less than or equal to about 270 bp, less than or equal to about 260 bp, less than or equal to about 250 bp, less than or equal to about 240 bp, less than or equal to about 230 bp, less than or equal to about 220 bp, less than or equal to about 210 bp, less than or equal to about 200 bp, less than or equal to about 195 bp, less than or equal to about 190 bp, less than or equal to about 185 bp, less than or equal to about 180 bp, less than or equal to about 175 bp, less than or equal to about 170 bp, less than or equal to about 165 bp, less than or equal to about 160 bp, less than or equal to about 155 bp, less than or equal to about 150 bp, less than or equal to about 145 bp, less than or equal to about 140 bp, less than or equal to about 135 bp, less than or equal to about 130 bp, less than or equal to about 125 bp, less than or equal to about 120 bp, less than or equal to about 115 bp, less than or equal to about 110 bp, less than or equal to about 105 bp, less than or equal to about 100 bp, or lower.

Any types of hybridization stabilizers known in the art or otherwise contemplated herein may be utilized in accordance with the present disclosure. In certain non-limiting embodiments, the hybridization stabilizer comprises a tail at the 5' end of at least one of the primers, wherein the tail comprises a sequence that is non-complementary to the target nucleic acid. In a particular (but non-limiting) embodiment, the tail comprises a sequence of G and/or C residues that is non-complementary to the target nucleic acid. For example (but not by way of limitation), the tail may comprise a GC-rich tail of about 2 residues, about 3 residues, about 4 residues, about 5 residues, about 6 residues, about 7 residues, about 8 residues, about 9 residues, about 10 residues, about 11 residues, about 12 residues, about 13 residues, about 14 residues, about 15 residues, about 16 residues, about 17 residues, about 18 residues, about 19 residues, about 20 residues, or higher, as well as a range in between two of these values (such as, but not limited to, a range of from about 3 to about 6 residues). In addition, the GC-rich tail may contain only G and C residues, or the GC-rich tail may simply have a higher GC-content than the remainder of the primer.

In another non-limiting embodiment, the hybridization stabilizer comprises the presence of at least one modified nucleotide in at least one of the amplification primers. Any type of modified nucleotides known in the art that can function as hybridization stabilizers may be utilized in accordance with the present disclosure. Non-limiting examples of chemically modified nucleotides that can be utilized as a hybridization stabilizer include C5-propynyl-dC (pdC), C5-propynyl-dU (pdU), and/or a locked nucleic acid (LNA). See, for example, U.S. Pat. No. 8,198,423 for use of pdU in probes.

In addition to the different initiation and propagation cycles present in the methods of the present disclosure, the plurality of amplification cycles may also include a single activation cycle that's performed prior to commencing the first initiation cycle. The activation cycle comprises a single hold step at a temperature for an initial time period. The temperature of the activation cycle may be at least about 85° C., at least about 86° C., at least about 87° C., at least about 88° C., at least about 89° C., at least about 90° C., at least about 91° C., at least about 92° C., at least about 93° C., at least about 94° C., at least about 95° C., or higher, and the temperature may be held for at least about 15 seconds, at least about 30 seconds, at least about 45 seconds, at least about 1 minute, at least about 1.5 minutes, at least about 2 minutes, at least about 2.5 minutes, at least about 3 minutes, at least about 3.5 minutes, at least about 4 minutes, at least about 4.5 minutes, at least about 5 minutes, at least about 5.5 minutes, at least about 6 minutes, at least about 6.5 minutes, at least about 7 minutes, at least about 7.5 minutes, at least about 8 minutes, or higher. For example (but not by way of limitation), the activation cycle may comprise a single hold step at a temperature greater than or equal to about 90° C. held for about 1 to about 5 minutes.

The thermocycling profile of the initiation cycle of the methods of the present disclosure may be provided with any temperature and time parameters so long as the cycle can function in accordance with the present disclosure. For example, but not by way of limitation, the thermocycling profile of the at least one initiation cycle may include a denaturation temperature of about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., or higher, as well as a range formed of any of the above values (such as, but not limited to, a range of from about 90° C. to about 100° C.). In addition, this temperature may be held for about 1 second, about 2 seconds, about 3 seconds, about 4 seconds, about 5 seconds, about 6 seconds, about 7 seconds, about 8 seconds, about 9 seconds, about 10 seconds, about 11 seconds, about 12 seconds, about 13 seconds, about 14 seconds, about 15 seconds, about 16 seconds, about 17 seconds, about 18 seconds, about 19 seconds, about 20 seconds, or higher, as well as a range formed of any of the above values (such as, but not limited to, a range of from about 2 to about 15 seconds). Similarly, the thermocycling profile of the at least one initiation cycle may have an elongation temperature of about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., or higher, as well as a range formed of any of the above values (such as, but not limited to, a range of from about 55° C. to about 65° C.). In addition, this temperature may be held for about 1 second, about 2 seconds, about 3 seconds, about 4 seconds, about 5 seconds, about 6 seconds, about 7 seconds, about 8 seconds, about 9 seconds, about 10 seconds, about 11 seconds, about 12 seconds, about 13 seconds, about 14 seconds, about 15 seconds, about 16 seconds, about 17 seconds, about 18 seconds, about 19 seconds, about 20 seconds, about 21 seconds, about 22 seconds, about 23 seconds, about 24 seconds, about 25 seconds, about 26 seconds, about 27 seconds, about 28 seconds, about 29 seconds, about 30 seconds, about 31 seconds, about 32 seconds, about 33 seconds, about 34 seconds, about 35 seconds, about 36 seconds, about 37 seconds, about 38 seconds, about 39 seconds, about 40 seconds, or higher, as well as a range formed of any of the above values (such as, but not limited to, a range of from about 15 to about 30 seconds). Also, the initiation cycle may be repeated for as many times as required to obtain a desired amount of amplification of the amplicon. For example, but not by way of limitation, the method may include about 1 initiation cycle, about 2 initiation cycles, about 3 initiation cycles, about 4 initiation cycles, about 5 initiation cycles, about 6 initiation cycles, about 7 initiation cycles, about 8 initiation cycles, about 9 initiation cycles, about 10 initiation cycles, about 11 initiation cycles, about 12 initiation cycles, about 13 initiation cycles, about 14 initiation cycles, about 15 initiation cycles, or more, as well as a range formed of any of the above values (such as, but not limited to, a range of from about 3 to about 10 initiation cycles).

One of the goals of optimization of the PCR methods of the present disclosure is to minimize the difference between the denaturation and elongation temperatures of the propagation cycles to increase the speed of the assay while maintaining sensitivity and specificity of the assay. For example, but not by way of limitation, the denaturation and elongation temperatures in the at least one propagation cycle vary from one another by about 35° C. or less, by about 34° C. or less, by about 33° C. or less, by about 32° C. or less, by about 31° C. or less, by about 30° C. or less, by about 29° C. or less, by about 28° C. or less, by about 27° C. or less, by about 26° C. or less, by about 25° C. or less, by about 24° C. or less, by about 23° C. or less, by about 22° C. or less, by about 21° C. or less, by about 20° C. or less, by about 19° C. or less, by about 18° C. or less, by about 17° C. or less, by about 16° C. or less, by about 15° C. or less, by about 14° C. or less, by about 13° C. or less, by about 12° C. or less, by about 11° C. or less, by about 10° C. or less, or lower.

The thermocycling profile of the propagation cycle of the methods of the present disclosure may be provided with any temperature and time parameters so long as the cycle can function in accordance with the present disclosure. For example, but not by way of limitation, the thermocycling profile of the at least one propagation cycle may include a denaturation temperature of about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., or higher, as well as a range formed of any of the above values (such as, but not limited to, a range of from about 80° C. to about 95° C., a range of from about 85° C. to about 95° C., etc.). In addition, this temperature may be held for about 1 second, about 2 seconds, about 3 seconds, about 4 seconds, about 5 seconds, about 6 seconds, about 7 seconds, about 8 seconds, about 9 seconds, about 10 seconds, about 11 seconds, about 12 seconds, about 13 seconds, about 14 seconds, about 15 seconds, or higher, as well as a range formed of any of the above values (such as, but not limited to, a range of from about 1 to about 5 seconds). Similarly, the thermocycling profile of the at least one propagation cycle may have an elongation temperature of about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., or higher, as well as a range formed of any of the above values (such as, but not limited to, a range of from about 60° C. to about 75° C.). In addition, this temperature may be held for about 1 second, about 2 seconds, about 3 seconds, about 4 seconds, about 5 seconds, about 6 seconds, about 7 seconds, about 8 seconds, about 9 seconds, about 10 seconds, about 11 seconds, about 12 seconds, about 13 seconds, about 14 seconds, about 15 seconds, about 16 seconds, about 17 seconds, about 18 seconds, about 19 seconds, about 20 seconds, or higher, as well as a range formed of any of the above values (such as, but not limited to, a range of from about 1 to about 15 seconds, a range of from about 5 to about 10 seconds, etc.). Also, the propagation cycle may be repeated for as many times as required to obtain a desired amount of amplification of the amplicon. For example, but not by way of limitation, the method may include about 10 propagation cycles, about 15 propagation cycles, about 20 propagation cycles, about 25 propagation cycles, about 26 propagation cycles, about 27 propagation cycles, about 28 propagation cycles, about 29 propagation cycles, about 30 propagation cycles, about 31 propagation cycles, about 32 propagation cycles, about 33 propagation cycles, about 34 propagation cycles, about 35 propagation cycles, about 36 propagation cycles, about 37 propagation cycles, about 38 propagation cycles, about 39 propagation cycles, about 40 propagation cycles, about 41 propagation cycles, about 42 propagation cycles, about 43 propagation cycles, about 44 propagation cycles, about 45 propagation cycles, about 46 propagation cycles, about 47 propagation cycles, about 48 propagation cycles, about 49 propagation cycles, about 50 propagation cycles, or more, as well as a range formed of any of the above values (such as, but not limited to, a range of from about 30 to about 45 initiation cycles, a range of from about 33 to about 40 propagation cycles, etc.).

In certain non-limiting embodiments, at least one of the primers utilized in the reaction comprises a detectable label. Any detectable labels known in the art for utilization in PCR assays may be utilized in accordance with the present disclosure. In one non-limiting embodiment, the detectable label is a fluorescent label.

In certain non-limiting embodiments, the entire amplification reaction (including all activation, initiation, and propagation cycles) is performed in less than about 25 minutes, such as (but not limited to), less than about 24 minutes, less than about 23 minutes, less than about 22 minutes, less than about 21 minutes, less than about 20 minutes, less than about 19 minutes, less than about 18 minutes, less than about 17 minutes, less than about 16 minutes, less than about 15 minutes, less than about 14 minutes, or less, as well as any range between two of the above values (i.e., a range of from about 15 minutes to about 20 minutes, etc.).

Certain non-limiting embodiments of the present disclosure are directed to a method of detecting a target nucleic acid in a biological sample. The method incudes any of steps (i) and (ii) described herein above, as well as step (iii) detecting the presence of the amplified target nucleic acid using a probe.

In certain non-limiting embodiments, the probe comprises at least one modified nucleotide. Any type of modified nucleotides known in the art that can function as hybridization stabilizers may be utilized in accordance with the present disclosure. Non-limiting examples of chemically modified nucleotides that can be included in the probe include C5-propynyl-dC (pdC), C5-propynyl-dU (pdU), and/or a locked nucleic acid (LNA). Alternatively (and/or in addition thereto), the probe may comprise at least one minor groove binder (MGB) moiety at a 3' end thereof.

Certain non-limiting embodiments of the present disclosure are directed to a reaction mixture for performing polymerase chain reaction on a biological sample suspected of containing a target nucleic acid (and in particular (but not by way of limitation), for performing any of the methods described or otherwise contemplated herein). The reaction mixture includes at least one thermostable polymerase (which can be any of the thermostable polymerases well known in the art or described or otherwise contemplated herein); nucleotides; and a pair of primers configured for amplification of the target nucleic acid. At least one of the primers comprises any of the hybridization stabilizers described or otherwise contemplated herein. In an optional embodiment, the reaction mixture may further comprise at least one of any of the probes described or otherwise contemplated herein.

For example (but not by way of limitation), the hybridization stabilizer may comprise a tail at the 5' end of at least one of the primers, wherein the tail comprises a sequence that is non-complementary to the target nucleic acid. In a particular (but non-limiting) embodiment, the tail comprises a sequence of G and/or C residues that is non-complementary to the target nucleic acid. For example (but not by way of limitation), the tail may comprise a GC-rich tail of about 2 residues, about 3 residues, about 4 residues, about 5 residues, about 6 residues, about 7 residues, about 8 residues, about 9 residues, about 10 residues, about 11 residues, about 12 residues, about 13 residues, about 14 residues, about 15 residues, about 16 residues, about 17 residues, about 18 residues, about 19 residues, about 20 residues, or higher, as well as a range in between two of these values (such as, but not limited to, a range of from about 3 to about 6 residues). In addition, the GC-rich tail may contain only G and C residues, or the GC-rich tail may simply have a higher GC-content than the remainder of the primer.

In another non-limiting embodiment, the hybridization stabilizer comprises the presence of at least one modified nucleotide in at least one of the amplification primers. Any type of modified nucleotides known in the art that can function as hybridization stabilizers may be utilized in accordance with the present disclosure. Non-limiting examples of chemically modified nucleotides that can be utilized as a hybridization stabilizer include C5-propynyl-dC (pdC), C5-propynyl-dU (pdU), and/or a locked nucleic acid (LNA). See, for example, U.S. Pat. No. 8,198,423 for use of pdU in probes.

In certain non-limiting embodiments, at least one of the primers present in the reaction mixture comprises a detectable label. Any detectable labels known in the art for utilization in PCR assays may be utilized in accordance with the present disclosure. In one non-limiting embodiment, the detectable label is a fluorescent label.

The amplicon comprising the target nucleic acid may possess any denaturation temperature and any length so long as the amplicon can be produced by the methods disclosed herein. For example (but not by way of limitation), the amplicon may have a full denaturation temperature of about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., or higher. In addition, the amplicon may have a full denaturation temperature that falls within a range formed of any of the above referenced values (such as, but not limited to, a range of from about 85° C. to about 95° C., a range of from about 85° C. to about 92° C., etc.). Non-limiting examples of amplicon length include, but are not limited to, less than or equal to about 300 bp, less than or equal to about 290 bp, less than or equal to about 280 bp, less than or equal to about 270 bp, less than or equal to about 260 bp, less than or equal to about 250 bp, less than or equal to about 240 bp, less than or equal to about 230 bp, less than or equal to about 220 bp, less than or equal to about 210 bp, less than or equal to about 200 bp, less than or equal to about 195 bp, less than or equal to about 190 bp, less than or equal to about 185 bp, less than or equal to about 180 bp, less than or equal to about 175 bp, less than or equal to about 170 bp, less than or equal to about 165 bp, less than or equal to about 160 bp, less than or equal to about 155 bp, less than or equal to about 150 bp, less than or equal to about 145 bp, less than or equal to about 140 bp, less than or equal to about 135 bp, less than or equal to about 130 bp, less than or equal to about 125 bp, less than or equal to about 120 bp, less than or equal to about 115 bp, less than or equal to about 110 bp, less than or equal to about 105 bp, less than or equal to about 100 bp, or lower.

When present, the probe may comprise, in certain non-limiting embodiments, at least one modified nucleotide. Any type of modified nucleotides known in the art that can function as hybridization stabilizers may be utilized in accordance with the present disclosure. Non-limiting examples of chemically modified nucleotides that can be included in the probe include C5-propynyl-dC (pdC), C5-propynyl-dU (pdU), and/or a locked nucleic acid (LNA). Alternatively (and/or in addition thereto), in certain non-limiting embodiments, the probe may comprise at least one minor groove binder (MGB) moiety at a 3' end thereof.

EXAMPLES

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

Example 1: Sculptural PCR Profiles Utilized in Fast PCR

Typical PCR methods have "monolithic profiles," where all of the PCR cycles are the same (i.e., same times, same temperatures, same ramp rates are utilized). There is no adjustment of the thermal profile to match the changing types and concentrations of nucleic acids during the PCR process. As such, monolithic PCR profiles are a compromise between the needs and properties of each phase of PCR. Because of the lack of adjustments to the thermal profile, these PCR methods exhibit longer times and lower sensitivities than ultimately desired.

In contrast, the term "sculptural PCR profiles" has been coined here to describe the PCR methods disclosed or otherwise contemplated herein. Sculptural methods allow the thermocycling profile to be modified to match the types and concentrations of nucleic acids at each phase of the PCR reaction. As such, different time and temperature regimes are utilized during the PCR reaction. The Sculptural PCR Profiles of the present disclosure allow for individual optimization of the different phases of the PCR reaction to deliver needed performance at every phase of the reaction. Because of the ability to adjust the various phases, the methods disclosed herein provide higher speeds, higher specificities, and higher sensitivities over the prior art methods.

One non-limiting embodiment of the adaptation of PCR Phases to Fast PCR conditions includes the following.

There are at least two phases of PCR amplification, and each of these phases is adapted.

The first phase is Initiation, and this phase includes target genomic DNA denaturation, primer binding, and extension on template. The initiation phase involves a high temperature denaturation (such as, but not limited to, 95° C. for five (5) seconds), followed by low temperature primer binding (such as, but not limited to, about 60° C.) with a long extension time (such as, but not limited to, about 20 seconds). This phase includes repetition of the high temperature denaturation and low temperature primer binding steps for about five (5) to about seven (7) cycles.

The second phase is Propagation, and this phase includes efficient exponential amplification of double stranded amplicons, with probe degradation and detection in late cycles. In this step, the difference between the denaturation temperature and the extension temperature is minimized (such as, but not limited to, to a difference of about 20° C. or less), so that the total time of the cycle can also be minimized. For example (but not by way of limitation), the denaturation temperature is driven by the $T_{den}$ of the amplicon, with a target $T_{den}$ in a range of from about 85° C. to about 90° C., and with a target period of about 2 seconds at this temperature; a high extension temperature ($T_{extend}$) is desired, with a target of about 70° C. and a short extension time of about 10 seconds. Optimization of the $T_{extend}$ also makes use of the optimal extension rate of polymerases (which is typically around 70° C., i.e., 10° C. above where most PCRs are carried out). This propagation phase includes repetition of the denaturation and extension steps for about 40 cycles.

Other optional steps may be performed before the initiation phase. For example (but not by way of limitation), an optional phase that could be performed prior to the initiation phase is Activation of a Hot Start polymerase, which includes a hot start and conversion of the inactive polymerase to an active form. This phase usually lasts in a range of from about one (1) to about five (5) minutes, is performed at or above about 90° C., and is a single event/cycle. This phase also includes antibody denaturation, aptamer melting, and/or anhydride derivative removal. This optional activation phase may be omitted if the polymerase used does not require the hot start component.

Another optional phase that may be performed before the initiation phase is a reverse transcription step. This step would be required if the nucleic acid target is RNA rather than DNA, and thus needs to be reverse transcribed into cDNA to provide a double stranded target molecule for amplification in the subsequent PCR reaction. Reverse transcription steps involve the use of reverse transcriptases and are very well known in the art; thus, no further description thereof is deemed necessary.

To obtain the higher speeds, higher specificities, and higher sensitivities desired for the methods of the present disclosure there are several goals for PCR profile optimization. First, the temperature gap between $T_{den}$ and $T_{extend}$ in the Propagation phase should be reduced as much as possible by using the lowest possible $T_{den}$ and the highest possible $T_{extend}$. Second, the time of $T_{den}$ should be reduced as much as possible to ideally provide only transient denaturation while still ensuring that the entire PCR volume is heated sufficiently. Third, the time of $T_{extend}$ should be reduced as much as possible; however, this reduction will ultimately be limited by the read times of the fluorescence detection channels. Finally, sufficiently high ramp rates need to be utilized to ensure rapid temperature transitions; however, the sufficiently high ramp rates still need to be lower than maximum ramp rates to extend the life of the system and improve system reliability and assay consistency.

Example 2: Design of Modified PCR Primers for Fast PCR

The Fast PCR methods of the present disclosure include the use of two unique features: the use of multiple thermocycling profiles that have been adjusted based on the amplicon (as discussed above in Example 1), and the use of a hybridization stabilizer. Two non-limiting embodiments of hybridization stabilizers—primers containing a GC-rich tail and a probe containing chemically modified nucleotides— that can be utilized in accordance with the present disclosure are described in this Example.

In this Example, a short amplicon of 103 bp is employed along with a conventional PCR primer sequence for initiation; however, each PCR primer includes a 5' non-complementary GC-rich tail to increase the $T_m$ during the propagation phase of the PCR reaction. As can be seen in Table 1 and FIG. 1, the addition of a GC-rich tail to the 5' end of each of the primers increased the $T_m$ by 9-11° C., to 71-75° C.

Similarly, this method also utilized a chemically modified detection probe. The term "BHQ+" stands for enhanced Black Hole Quencher probes (Biosearch Technologies, Novato, CA) and references the combination of Biosearch's BHQ quencher dye chemistry for probes along with the use of chemical modification of C and T residues (i.e., pdU and pdC modified nucleotides) in a method of oligonucleotide synthesis; BHQ+ probe synthesis modifies C's to pdC and provides a 1° C. stabilization per residue, while BHQ+ probe synthesis modifies T's to pdU and provides a 0.5° C. stabilization per residue. As shown in Table 1, the BHQ+ detection probe includes 9 pdU and 8 pdC, and as such, the presence of the modified bases increased the $T_m$ of the probe by 12.5° C. to 75.5° C.

TABLE 1

| Primer Sequence (GC-rich tails underlined) | SEQ ID NO: | Modification | Length | Core $T_m$ | Modified $T_m$ |
|---|---|---|---|---|---|
| GCGCCTGGATG TGTCTGCGGCG TTTTATCAT | 1 | 5' GC-rich tail | 26 | 66° C. | 75° C. |
| GGCGGGACAAA CGGGCAACATA CCTT | 2 | 5' GC-rich tail | 21 | 60° C. | 71° C. |
| ATCCTGCTGCT ATGCCTCATCT T | 3 | 9 pdU and 8 pdC | 23 | 63° C. | 75.5° C. |

Example 3: Optimization of Denaturation Temperatures for Fast PCR

There are two different types of denaturation required in a Fast PCR reaction: (1) denaturation of the target DNA, allowing initial primer extension; and (2) denaturation of the amplicon, during propagation phase. When the amplicon is selected to have a low $T_{den}$, a temperature overshoot at the end of the ramp is allowed. This temperature overshoot ensures compete denaturation in a short time and fast and efficient amplification and detection. The temperature overshoot also ensures temperature homogeneity in the PCR volume without thermally irreversibly denaturing the polymerase and allows for a single heating surface—thereby requiring a simpler, lower cost instrument. In addition, use of a lower temperature overshoot may reduce bubble formation and thus improve consistency.

For example, an HBV amplicon of SEQ ID NO:4 has a length of 216 bp and a $T_{den}$ of 92° C. When this amplicon was truncated to the sequence of SEQ ID NO:5, this 82 bp sequence now has a $T_{den}$ of 88° C. Then primers with GC-rich tails and a BHQ+ probe were created as described above in Example 2. Each of these sequences is shown in Table 2. It is noted that, in this particular (but non-limiting) example, the $T_m$ of the BHQ+ probe should be slightly higher than the primers.

TABLE 2

| Original 216 bp HBV amplicon (SEQ ID NO: 4) | CTCACAATACCGCAGAGTCTAGACTCGT GGTGGACTTCTCTCAATTTTCTAGGGGG AACTACCGTGTGTCTTGGCCAAAATTCG CAGTCCCCAACCTCCAATCACTCACCAA CCTCTTGTCCTCCAACTTGTCCTGGTTA TCGCTGGATGTGTCTGCGGCGTTTTATC ATCTTCCTCTTCATCCTGCTGCTATGCC TCATCTTCTTGTTGGTTCTT |
|---|---|
| Truncated 82 bp HBC amplicon (SEQ ID NO: 5) | gcgccTGGATGTGTCTGCGGCGTTTTAT CATCTTCCTCTTCATCCTGCTGCTATGC CTCATCTTCTTGTTGGTTCTTCTGGACT ATCAAGGTATGTTGCCCGTTTGTCccgc c* |

| Primer Sequence (GC-rich tails underlined) | SEQ ID NO: | Modification | Length | Core T$_m$ | Modified T$_m$ |
|---|---|---|---|---|---|
| GGCGAGACT CGTGGTGGA CTTCTCTCA | 6 | 5' GC- rich tail | 27 | 63° C. | 69° C. |
| GGCGGCATA GCAGCAGGA TGCAGA | 7 | 5' GC- rich tail | 24 | 64° C. | 70° C. |
| TCTGCGGCG TTTTATCAT CTTCCTCTT | 8 | 13 pdU and 7 pdC | 27 | 63° C. | 76.8° C. |

*Underlined portions are derived from the GC tails on the primers, and thus are non-complementary to the HBV genome.

Thus, there are ways to optimize the PCR profile to make use of Fast PCR instrument capabilities. This optimized profile drives assay design features such as (but not limited to) amplicon length and primer and probe T$_m$. This optimized profile in turn challenges the bioinformatics analysis of target sequences to define regions and sequences which meet the desired assay specificity and sensitivity, and which also support the assay design needs for short amplicons.

Example 4: Propagation Phase—Optimization of Denaturation Temperature

This Example is related to the application of the features described in the previous Examples. The goals of this Example include: (1) the development of rapid PCR profiles to allow sensitive and accurate DNA amplification in under 20 minutes, and (2) the design of PCR profiles which deliver sufficient safety margins that allow tolerance to assay and engineering variation without inducing unsustainable stress on the instrument.

To meet these goals, and as described in detail herein below, the following steps were employed: (a) a two-phase PCR profile for DNA assay was developed (i.e., initiation and propagation phases); (b) the lowest tolerable T$_{den}$ and shortest duration time were defined to ensure efficient amplicon denaturation; (c) GC-tailed primers and BHQ+ probes were introduced to increase T$_m$ in the propagation phase; (d) the extension time was reduced while ensuring good signal generation; and (e) linearity and limit of detection (LoD) were verified with processed HBV targets.

First, to optimize T$_{den}$, a temperature gradient was utilized to set the lowest possible T$_{den}$, with the desire to close the gap between T$_{den}$ and T$_{ann/extend}$ as much as possible. Using a gradient of denaturation temperatures from 83-95° C., it was found that the optimal amplification was observed using 90° C. for two seconds for denaturation, followed by 10 seconds at 70° C. on the Fast QuantStudio 5 (Fast QS5) PCR System (ThermoFisher Scientific, Waltham, MA).

Profile optimization using the Fast QS5 instrument, HBV GC-tail primers, and denaturation temperature gradient involved the following experimental setup. HBV hybrid gBlock template was utilized. Serial dilution 10$^4$ copies/μl was tested. PCR was run in 10 μl total reaction volume and included the following: 1 μl sample, FTD MMX (5× buffer and 25× ENZ4), and 500 nM of the primers HBV_FB_pm1_GC and HBV_FB_pm2_GC, and 100 nM of the probe HBV_FB_PR_FAM_BHQ+. The PCR profile utilized is shown in Table 3.

TABLE 3

| Step | Profile #1 |
|---|---|
| Hold (temperature/time) | 95° C./1 min |
| Initiation phase (5 cycles) | |
| Denaturation (temperature/time) | 95° C./10 sec |
| Annealing & Amplification (temperature/time) | 60° C./20 sec |
| Propagation phase (35 cycles) | |
| Denaturation (temperature/time) | 83, 85, 88, 90, 93, or 95° C./2 sec |
| Annealing & Amplification (temperature/time) | 70° C./10 sec |
| Ramp rate | (4.82° C./s; 3.72° C.) |

Figure 2:
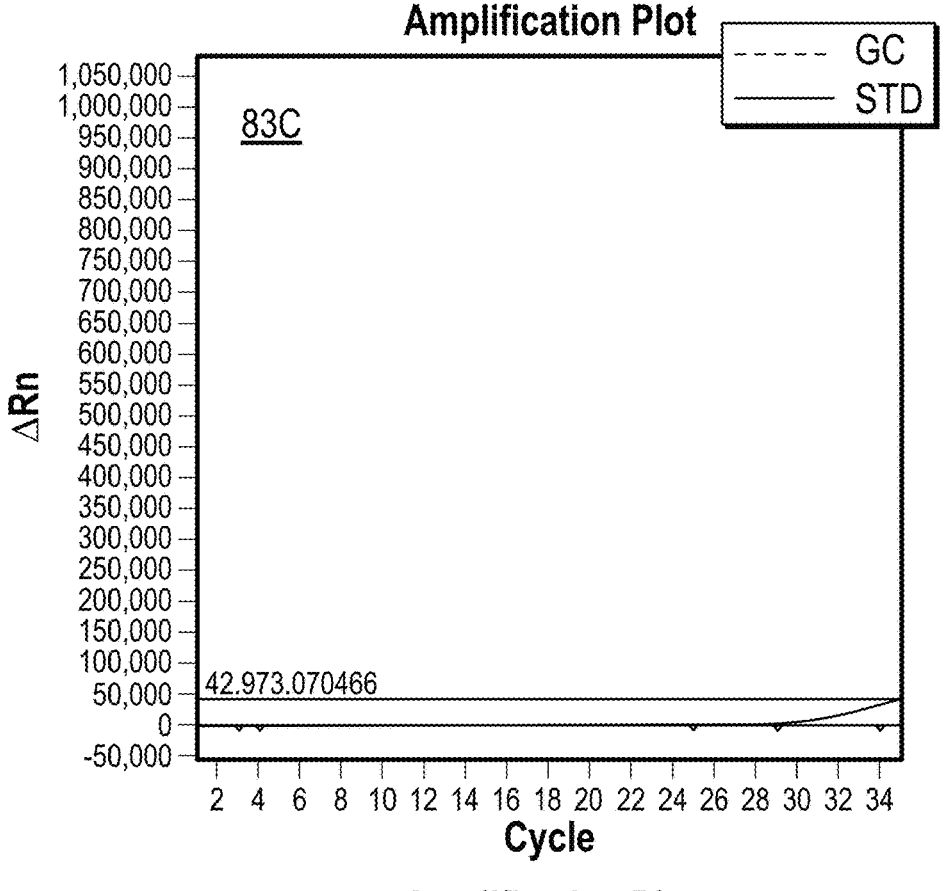
FIG. 2 contains amplification plots of PCR reactions using standard and GC-tailed primers across a denaturation temperature gradient.
Figure 2:
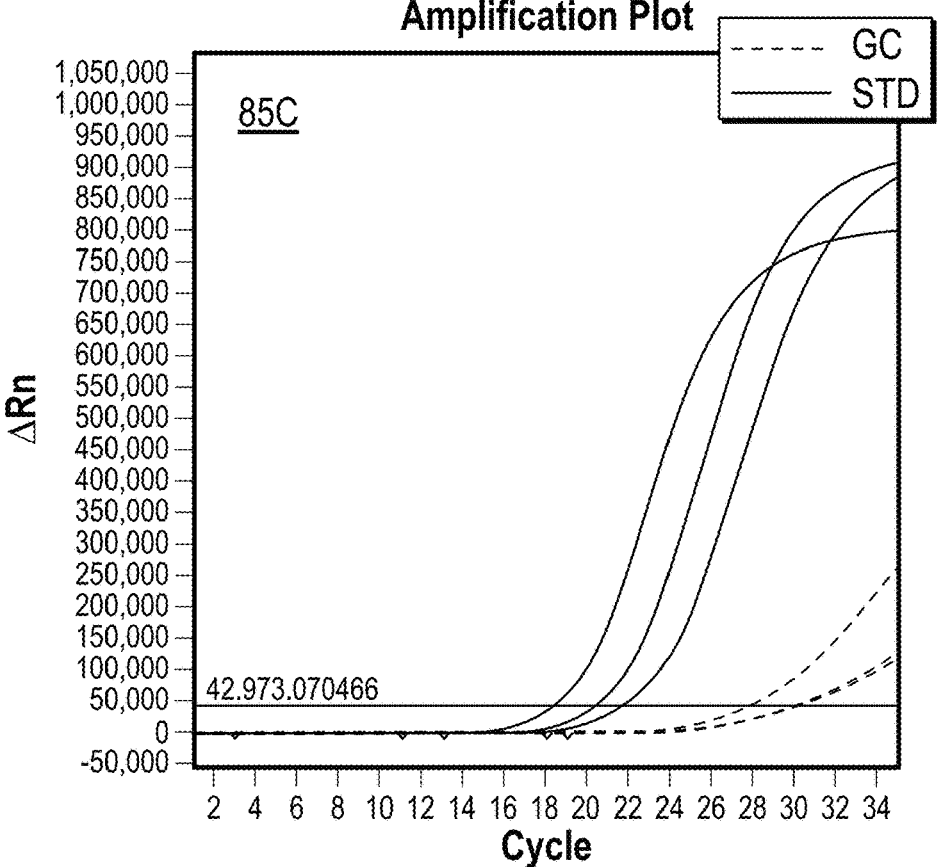
Figure 2:
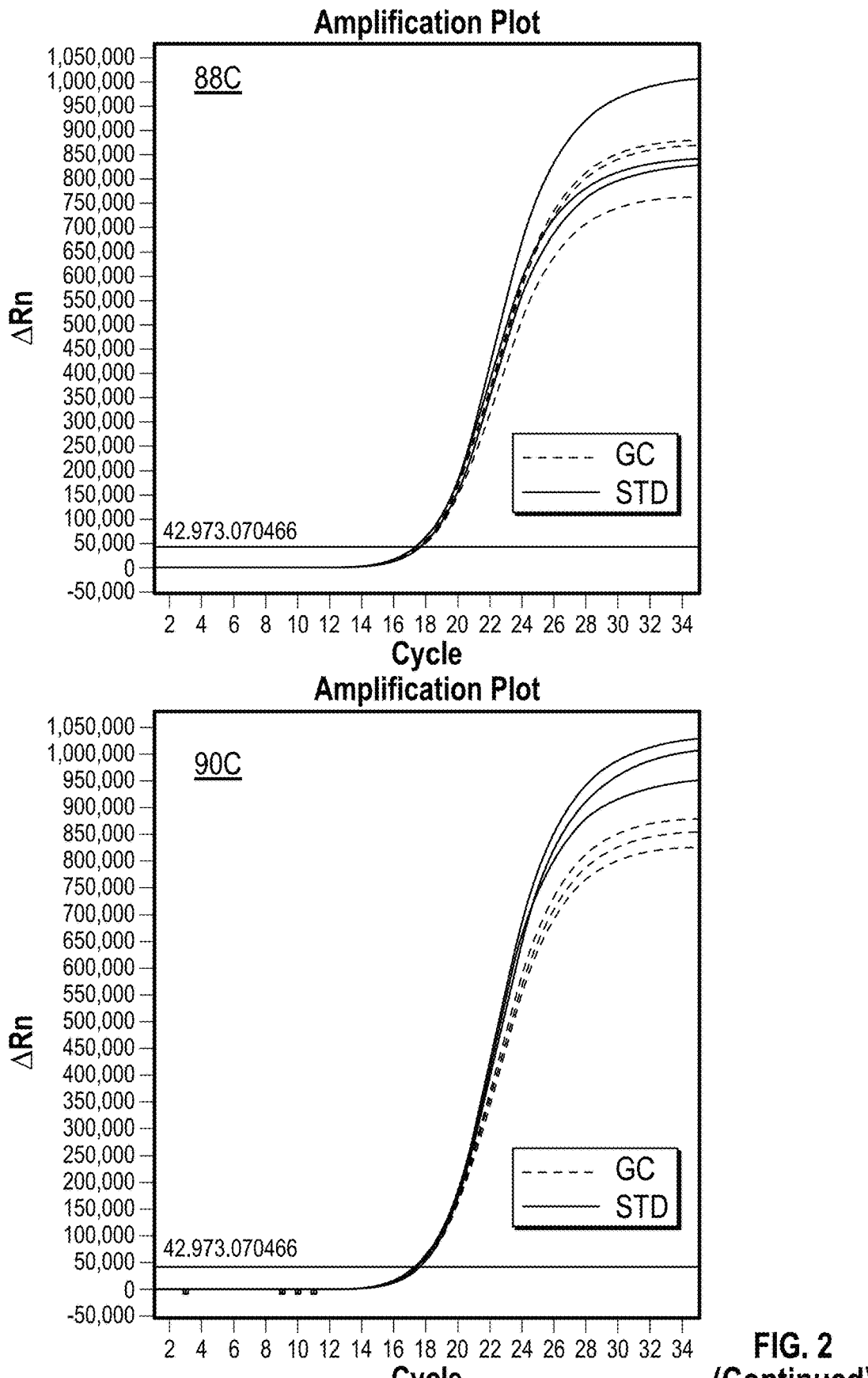
Figure 2:
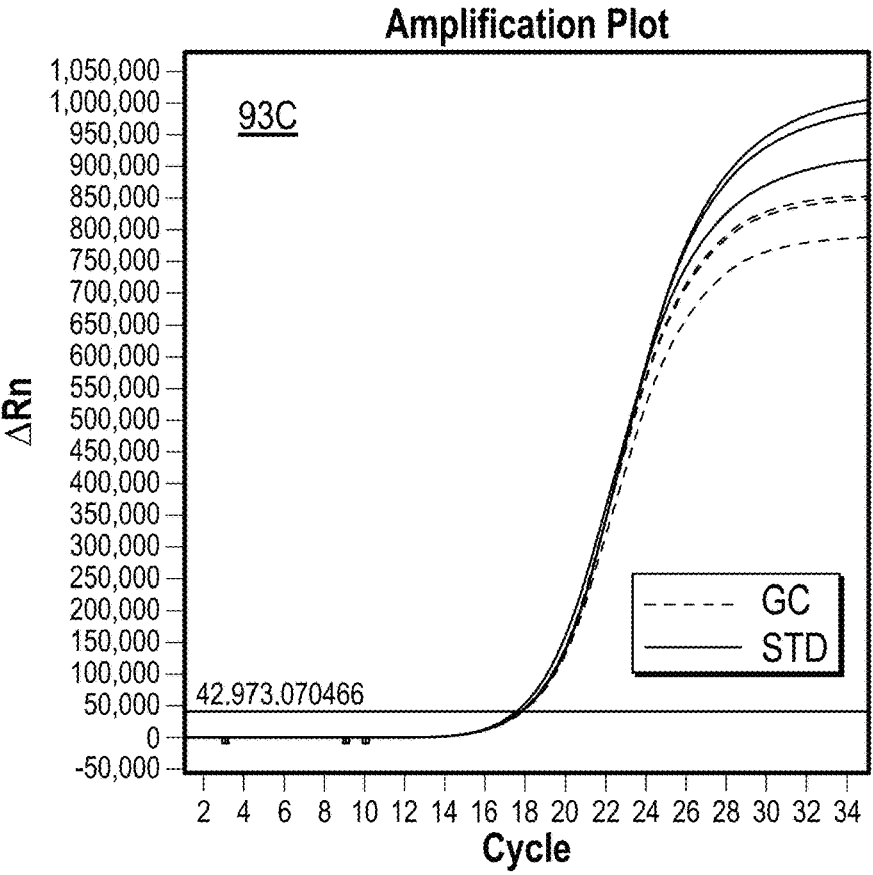
Figure 2:
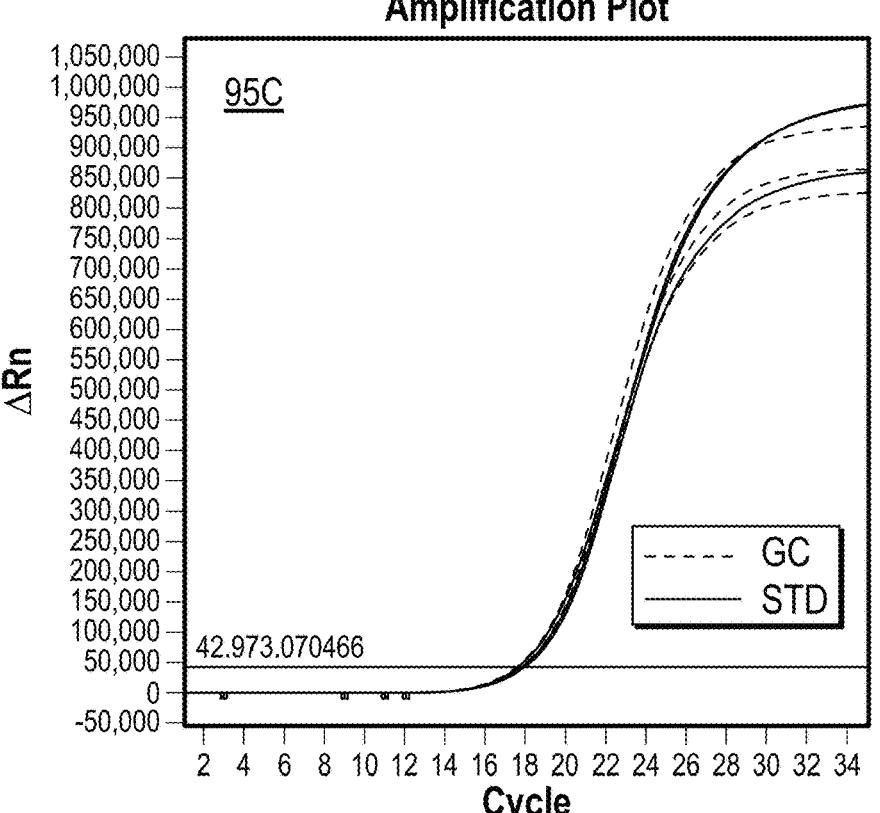

The results observed at the different denaturation temperatures are shown in FIG. 2. The results demonstrate that amplicons produced using standard primers have lower T$_{den}$ than amplicons produced with GC-tailed primers. In addition, when the denaturation temperature was increased, more templates with GC tails were denatured and more products generated. At 95° C., the performance of standard and GC-tail primers were similar. As such, the set point of 90° C. for denaturation was optimal for GC-tailed primers.

Figure 3:
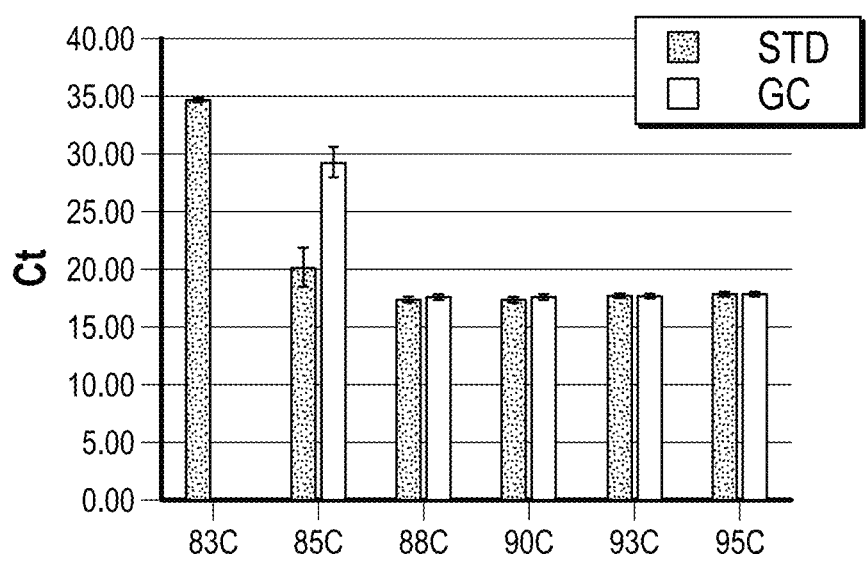
FIG. 3 contains an evaluation of Ct and dRn of PCR reactions using standard and GC-tailed primers across a denaturation temperature gradient. The term "Ct" refers to the PCR cycle at which a threshold level of fluorescence is reached, while the term "dRn" refers to a baseline subtracted fluorescence reading normalized to the reference dye.
Figure 3:
Figure 3:
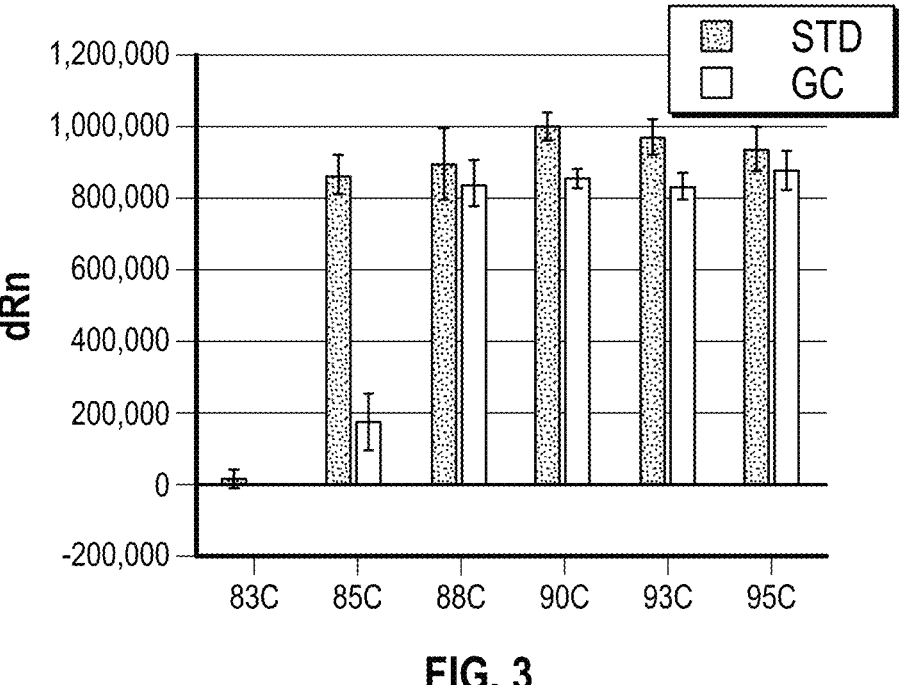

Also, as shown in FIG. 3, the Ct values of standard and GC-tailed primers were similar when using a denaturation temperature of 88-95° C.; however, the fluorescent intensity was slightly different.

Figure 4:
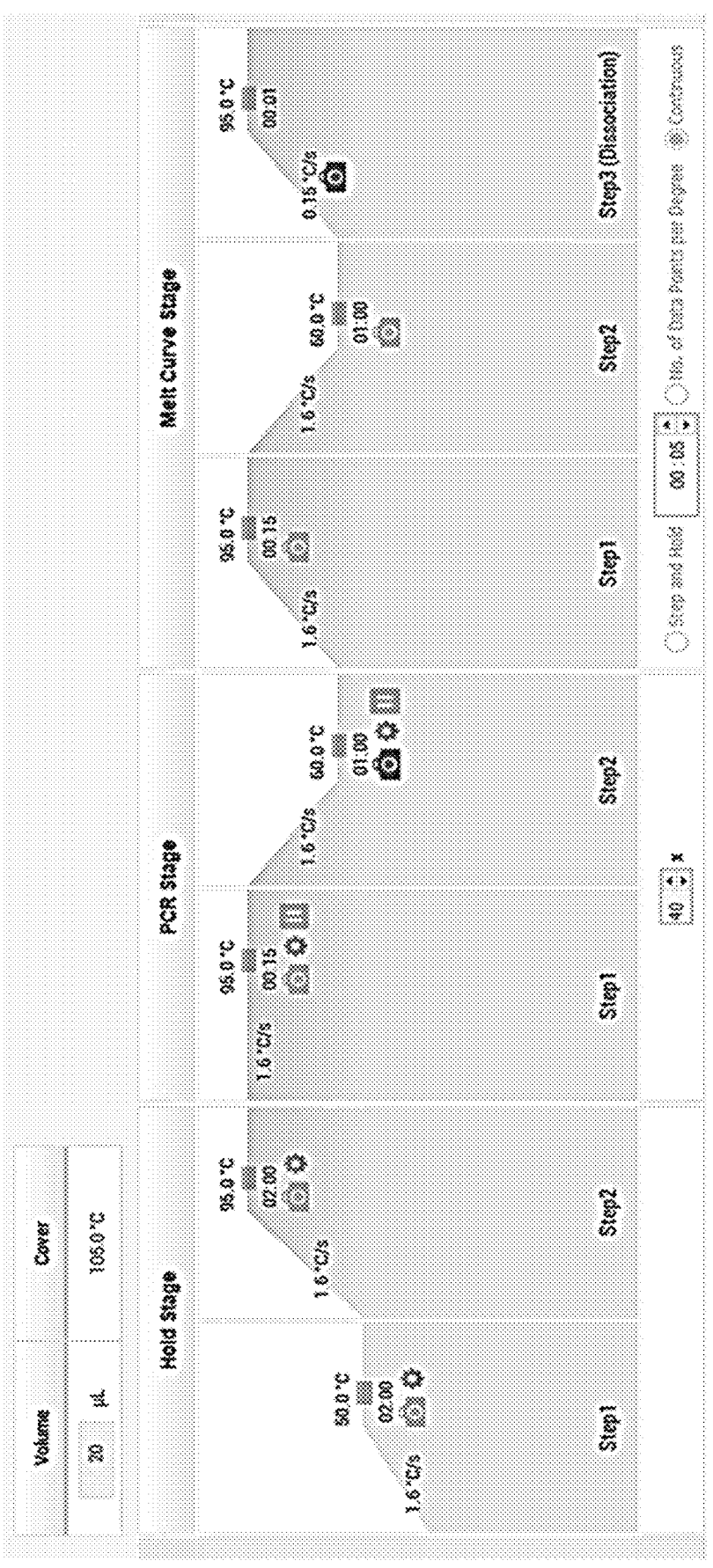
FIG. 4 contains an example of one PCR thermocycling profile constructed in accordance with the present disclosure.

To help define the target T$_{den}$ for respective target amplifications, the T$_{den}$ of amplicons for HCV and HBV of various lengths were measured. In this experiment, HBV hybrid and HCV 5'UTR gBlock templates truncated into different lengths were utilized, along with the experimental assay for products produced using standard and GC-tail primers. The PCR was performed in 20 μl total reaction volume with 1 μl sample and ThermoFisher 2× Power SYBR master mix and the primers outlined in Table 4. The PCR profiles are shown in FIG. 4.

TABLE 4

| Template | Forward primer | Reverse Primer |
|---|---|---|
| HBV gBlock | S_HBV_F | FTD_HBV_R |
| HBV STD | HBV_FB_pm1_std | FTD_HBV_R |
| HBV GC | HBV_FB_pm1_GC | HBV_FB_pm2_GC |
| HCV | HCV_2.0_Forward_Primer_1 | HCV_Reverse_Primer_1 |

Figure 5:
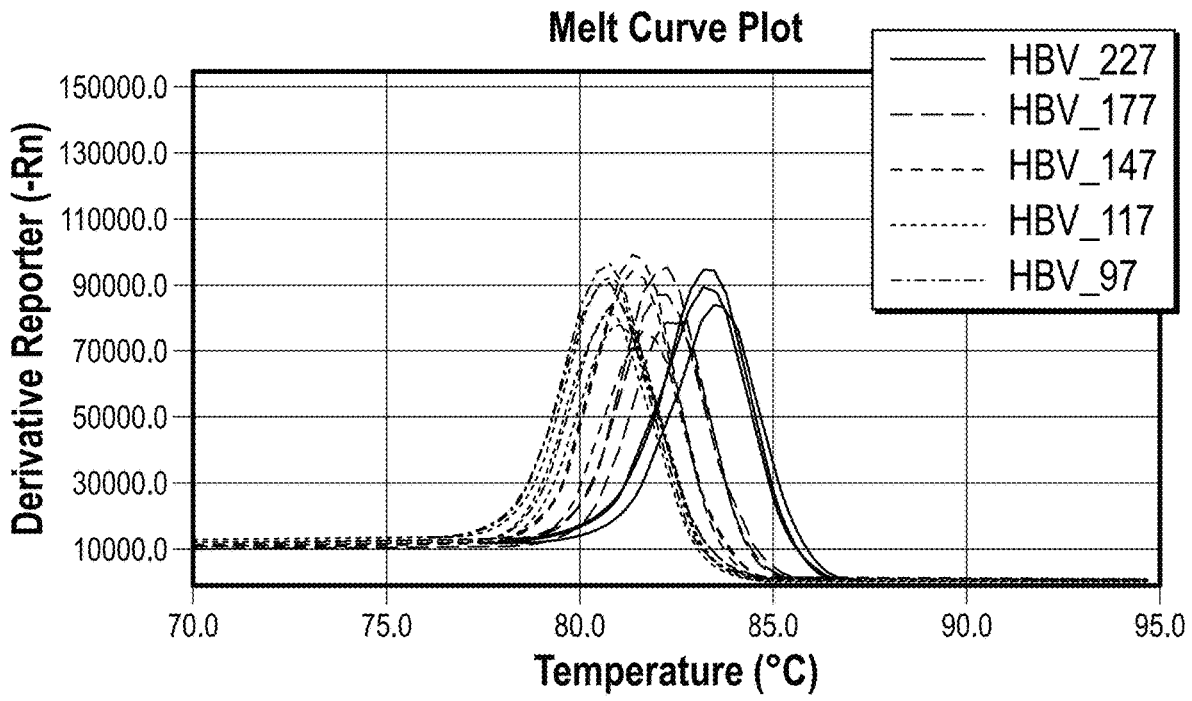
FIG. 5 contains melt curve plots for determining full denaturation temperatures of various HBV and HCV amplicons.
Figure 5:
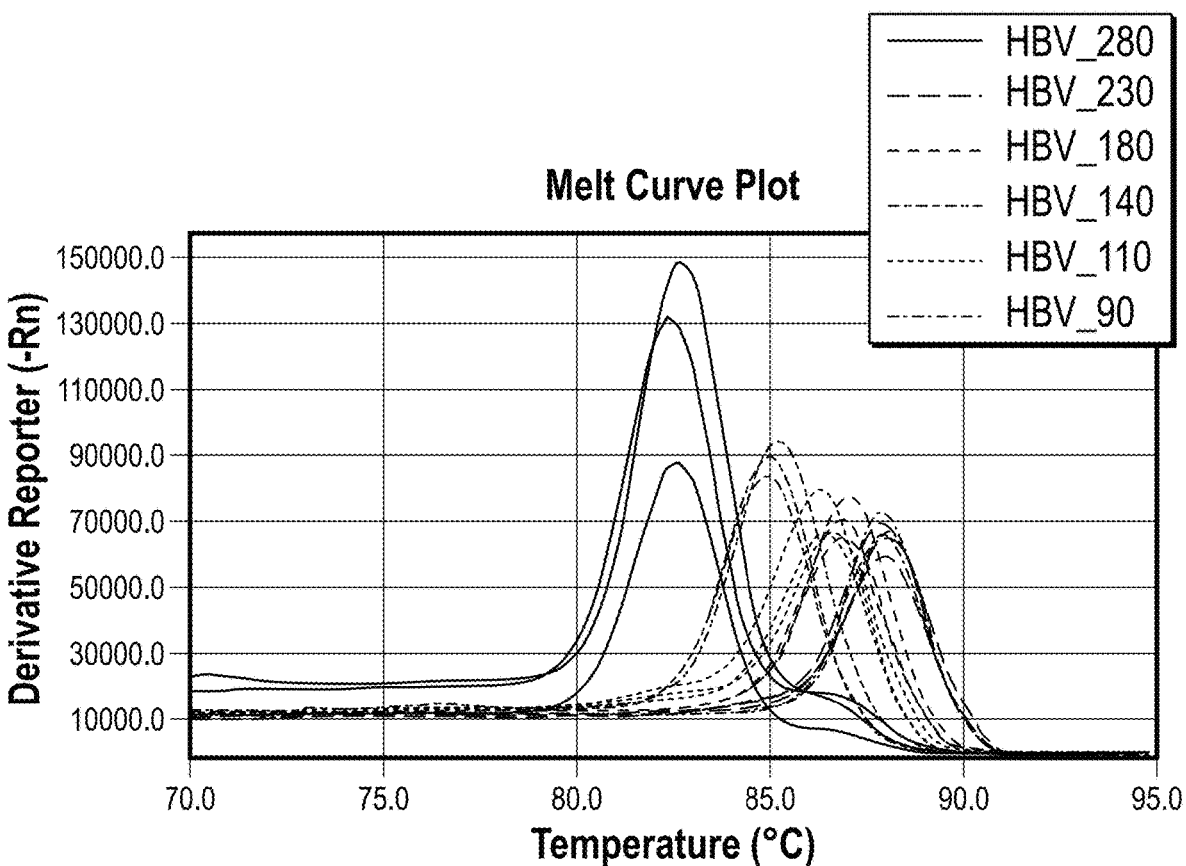
Figure 5:
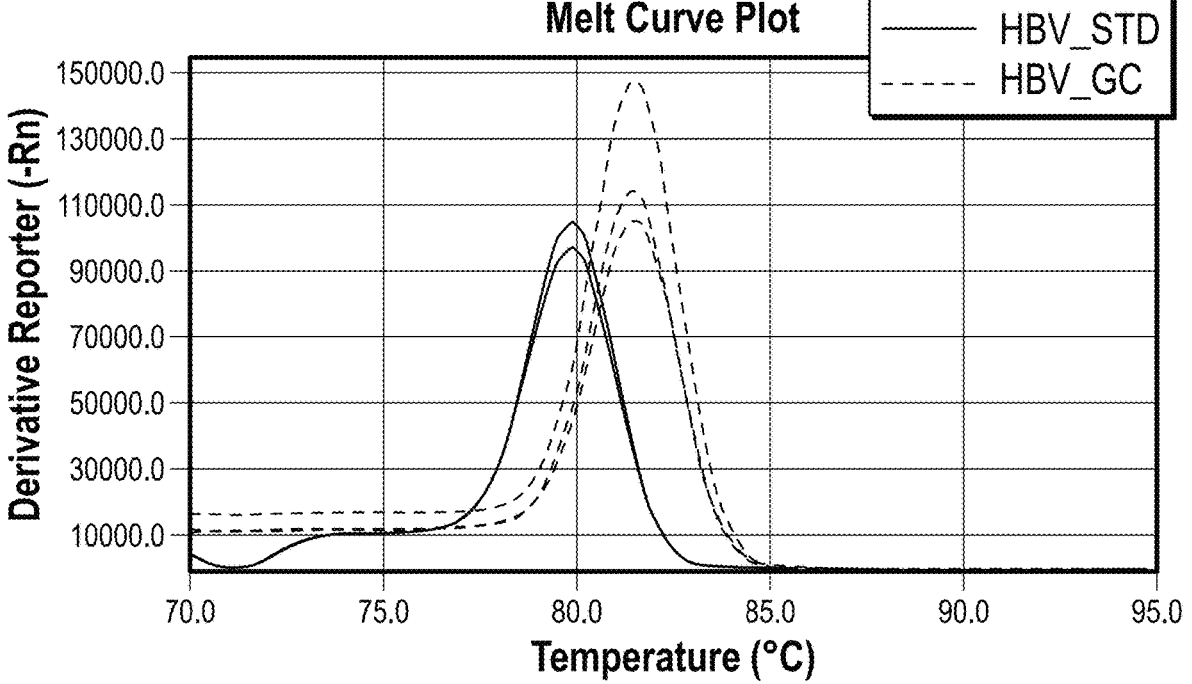

Table 5 lists the various templates utilized as well as the T$_m$ and full denaturation temperatures thereof, while FIG. 5 shows the various melt curve plots obtained with the various templates.

TABLE 5

| Template Description | Tm (° C.) | Full Denaturation |
|---|---|---|
| HBV Templates | | |
| HBV 227 bp | 83 | 90° C. |
| HBV 177 bp | 82 | |
| HBV 147 bp | 81.5 | |
| HBV 117 bp | 80.5 | |
| HBV 97 bp | 80.5 | |
| HBV STD 103 bp | 80 | |
| HBV GC 113 bp | 81.5 | |
| HCV Templates | | |
| HCV 280 bp | 88 | 93-95° C. |
| HCV 230 bp | 88 | |
| HCV 180 bp | 87 | |
| HCV 140 bp | 86.5 | |
| HCV 110 bp | 85 | |
| HCV 90 bp | 82.5 | |

As can be seen, HBV amplicons of 90 bp-227 bp were relatively similar in $T_{den}$, with a range of only 3° C. from 80° C.-83° C. The HCV amplicons showed a broader range of $T_{den}$ which vary according to length from 90 bp-280 bp (a range of 6° C. from 82.5° C.-88° C.), and driven by higher GC content. These $T_{den}$'s represent 50% denaturation, so high efficiency PCR would require higher temperatures to ensure sufficient denaturation. Thus, it is recommended to measure the $T_{den}$ of an assay's target amplicon to define the minimum set point $T_{den}$ for a PCR profile.

As such, the above demonstrates that the GC content of the amplicon (HBV has a relatively normal GC content, while HCV has a high GC content) influences assay performance.

Example 5: Propagation Phase—Optimization of Annealing/Amplification Temperature For optimizing annealing and amplification temperature gradient and duration, anneal/extend times of 5, 8, and 10 seconds at temperatures in a range of from 60° C.-75° C. were evaluated, along with a comparison of the standard versus GC-tailed primers using the same probe and the Fast QS5 instrument. It was found that GC primers functioned well up to at least 75° C. and in as short as 5 seconds, or even less. By minimizing the gap between the denaturation and annealing/amplification temperatures (in this case, a gap of 15° C. between 90° C. and 75° C. for denaturation and annealing/amplification temps, respectively), it was possible to minimize the amount of time required to maneuver between the two temperatures. In contrast, the standard primers were unable to amplify or had Ct delay when the extension temperature was above 70° C. However, when the extension temperature increased to 72° C.-75° C., the fluorescent signal slightly decreased in the GC-tail primers, thus demonstrating a thermal influence on fluorescence that should be taken into account under certain circumstances.

Profile optimization of the annealing/amplification temperature gradient using the Fast QS5 instrument and HBV GC-tail primers involved the same experimental setup as was used for optimization of the denaturation temperature, as described herein above in Example 4. The PCR profile utilized is shown in Table 6.

TABLE 6

| Step | Profile |
|---|---|
| Hold (temperature/time) | 95° C./1 min |
| Initiation phase (5 cycles) | |
| Denaturation (temperature/time) | 95° C./10 sec |
| Annealing & Amplification (temperature/time) | 60° C./20 sec |
| Propagation phase (35 cycles) | |
| Denaturation (temperature/time) | 90° C./2 sec |
| Annealing & Amplification (temperature/time) | 60, 65, 68, 70, 72, 75° C./ 5, 8, 10 sec |
| Ramp rate | (4.82° C./s; 3.72° C.) |

Figure 6:
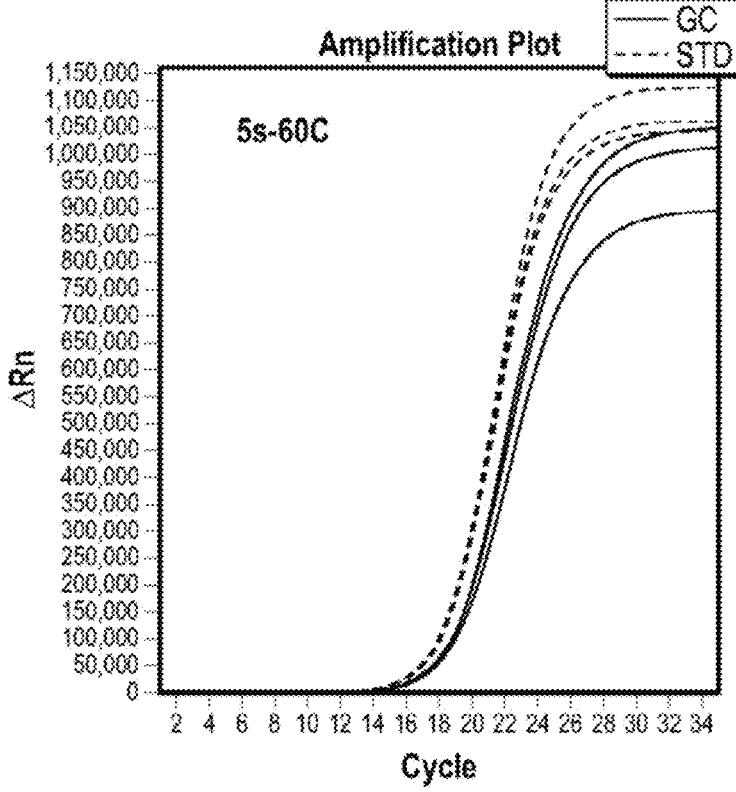
FIG. 6 contains amplification plots of PCR reactions using standard and GC-tailed primers across an annealing/amplification temperature gradient and at various duration times.
Figure 6:
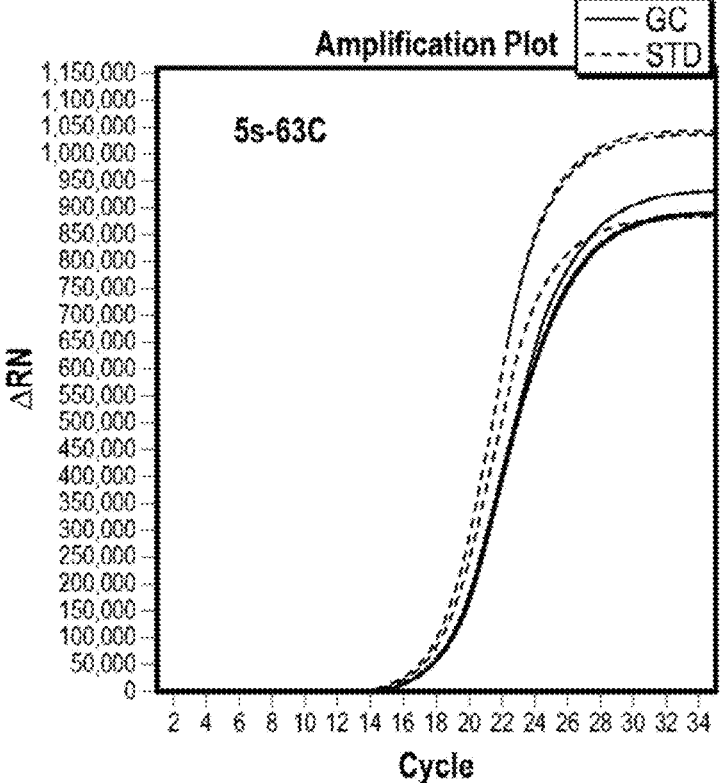
Figure 6:
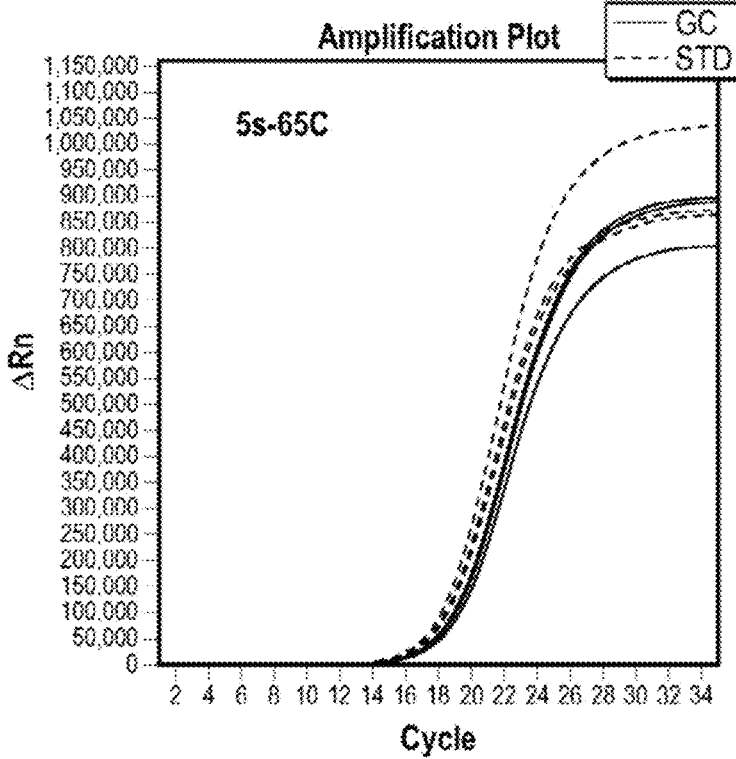
Figure 6:
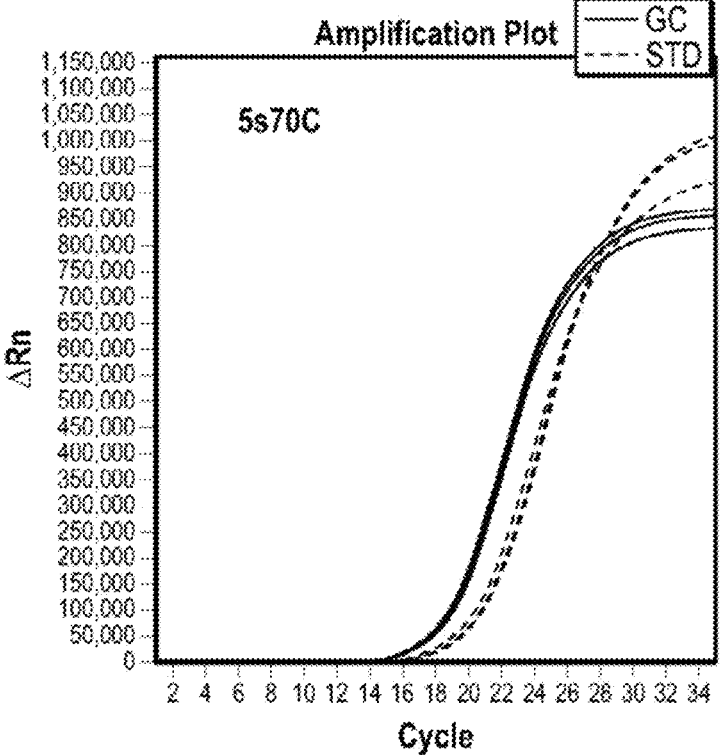
Figure 6:
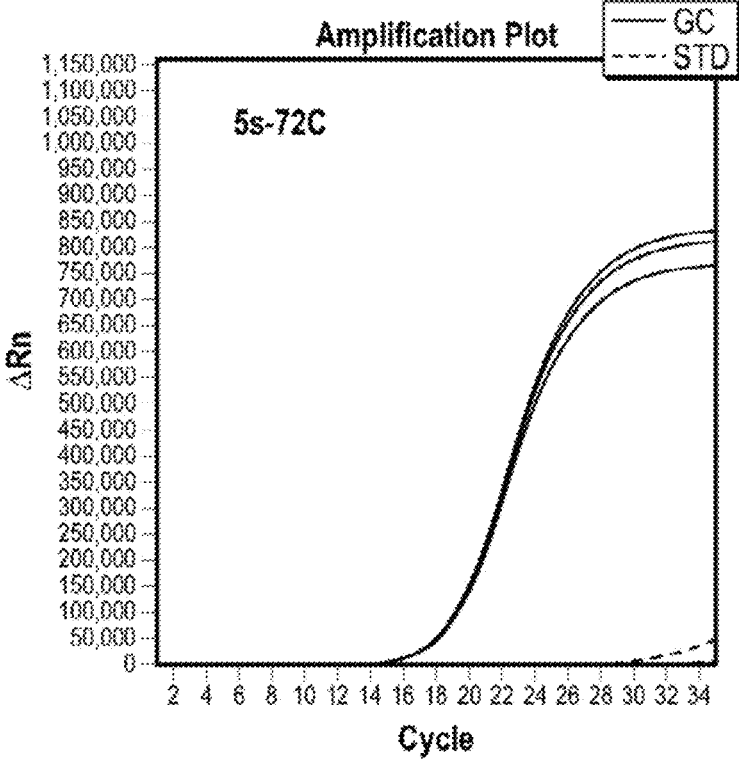
Figure 6:
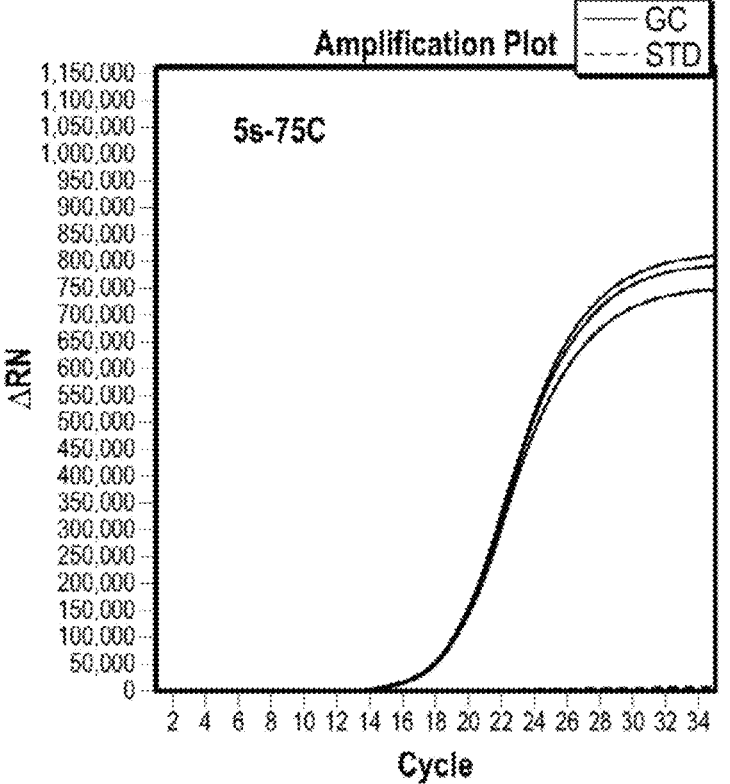
Figure 6:
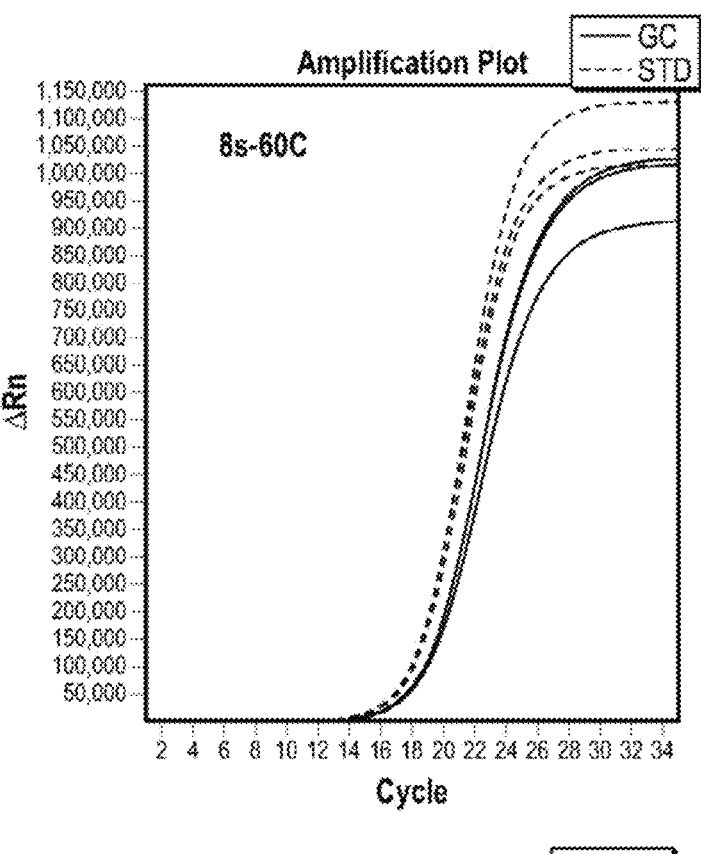
Figure 6:
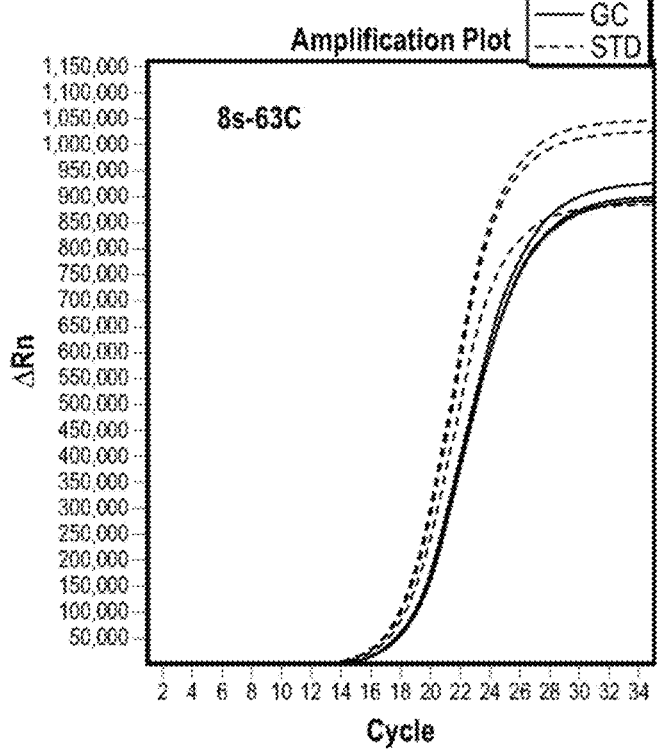
Figure 6:
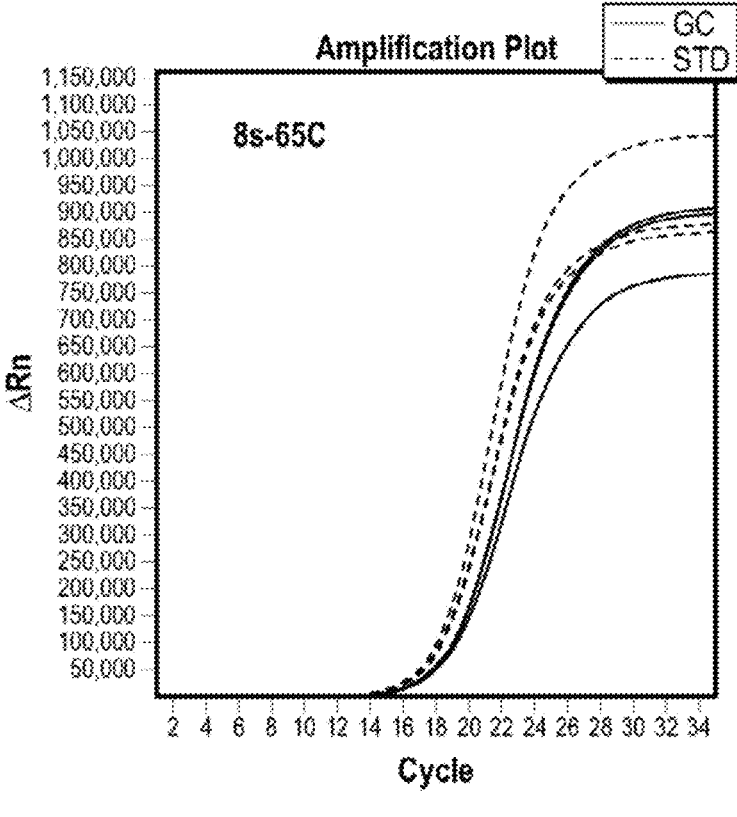
Figure 6:
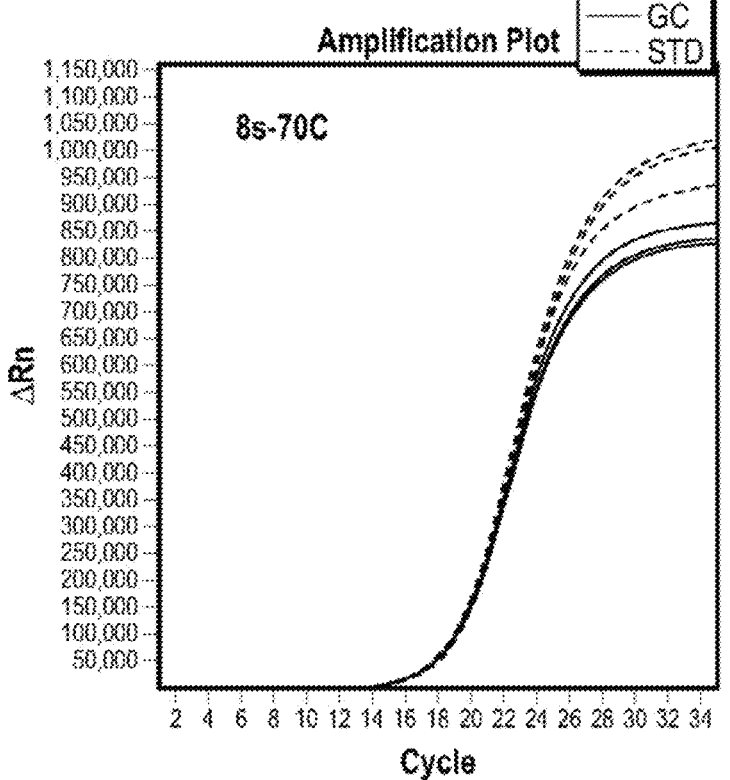
Figure 6:
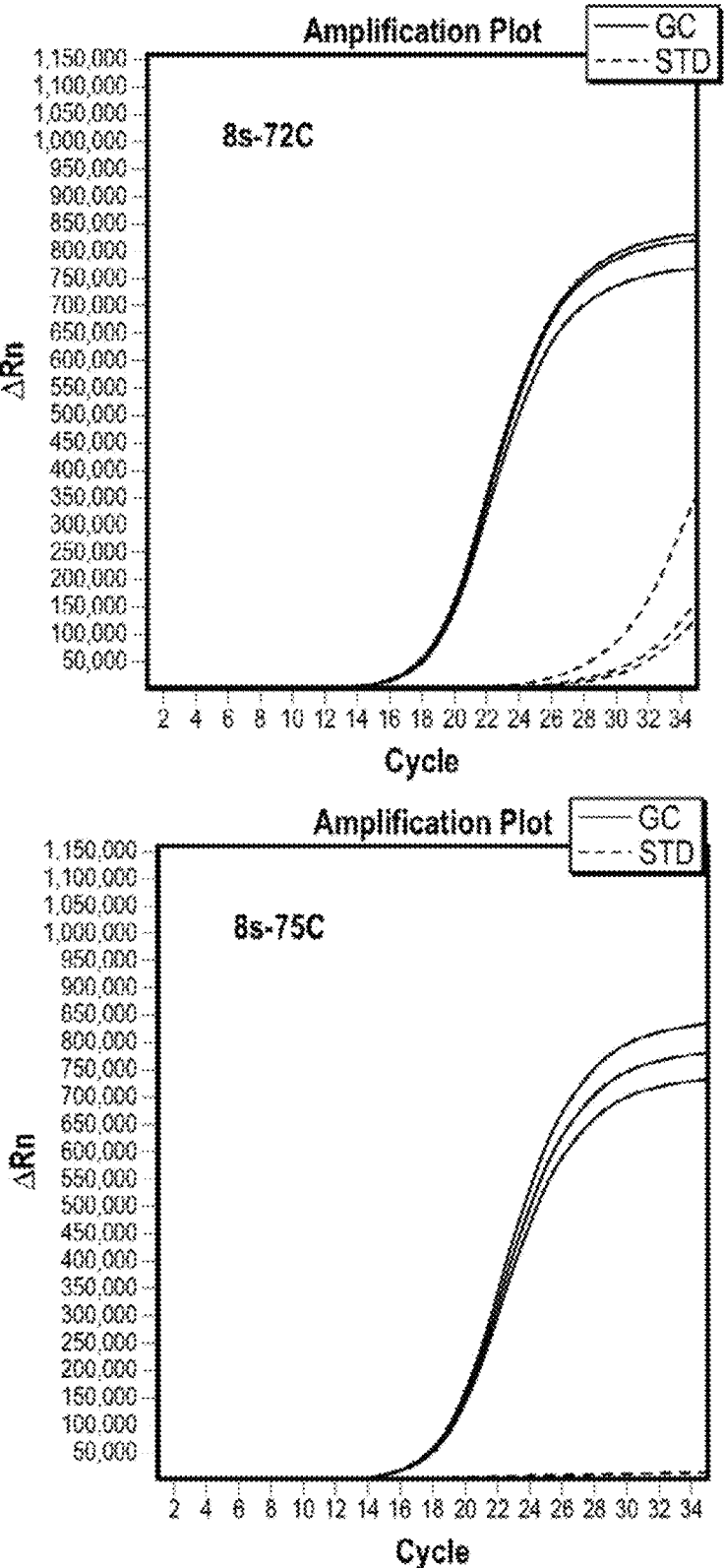
Figure 6:
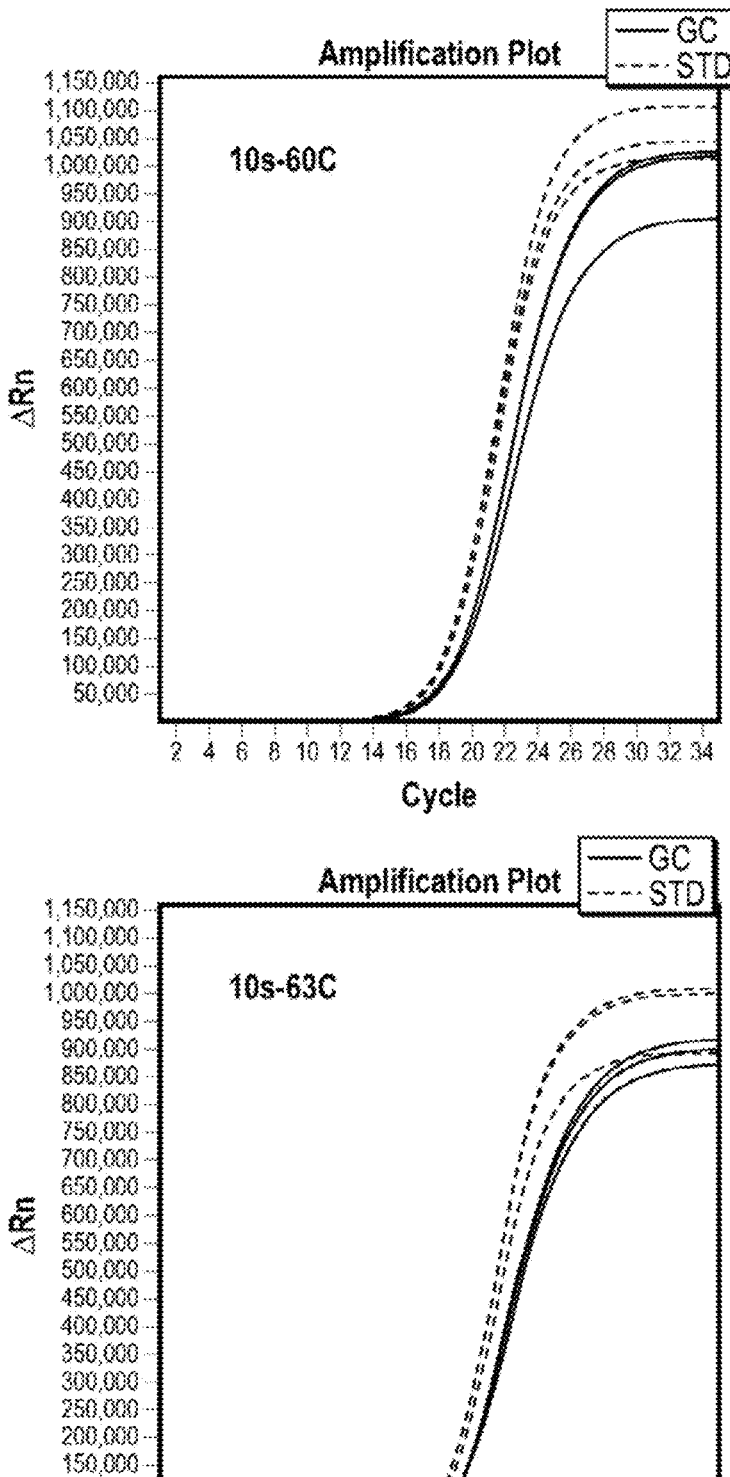
Figure 6:
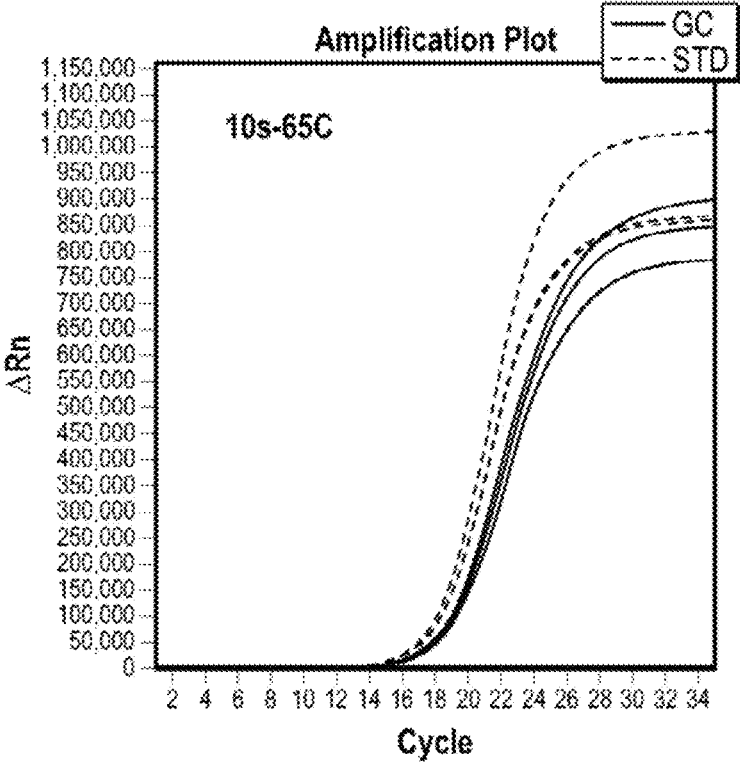
Figure 6:
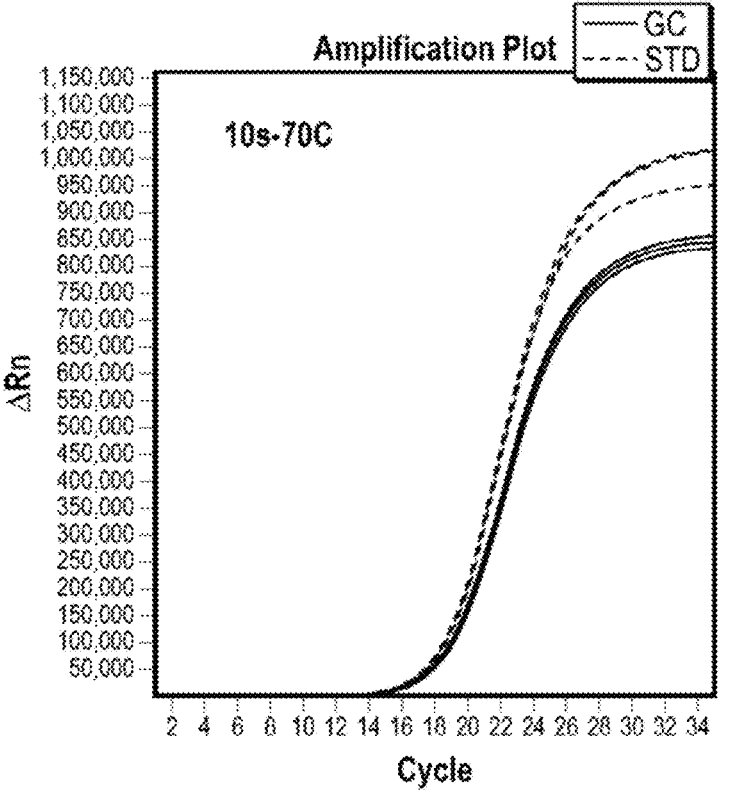
Figure 6:
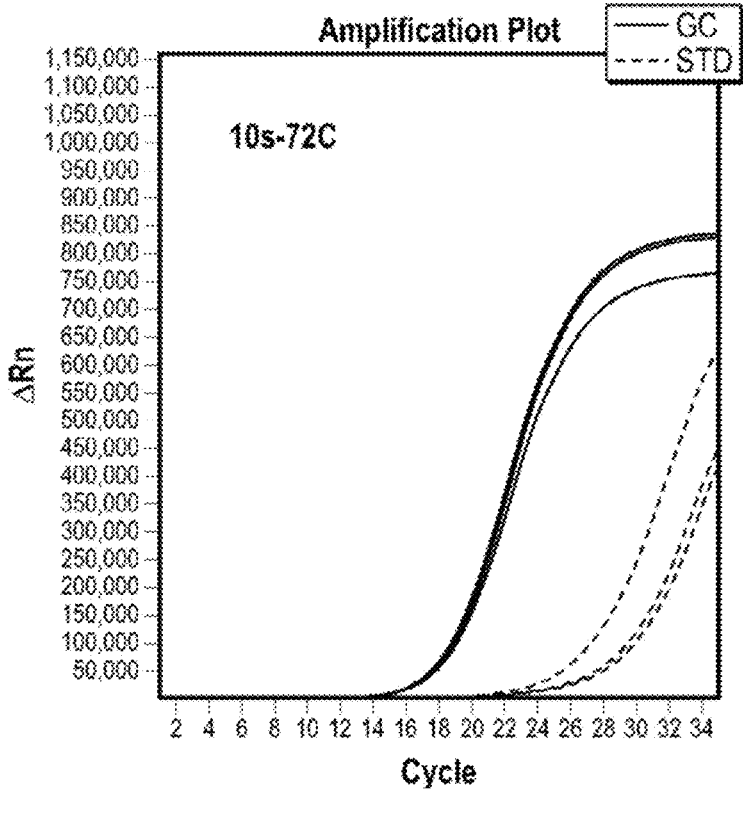
Figure 6:
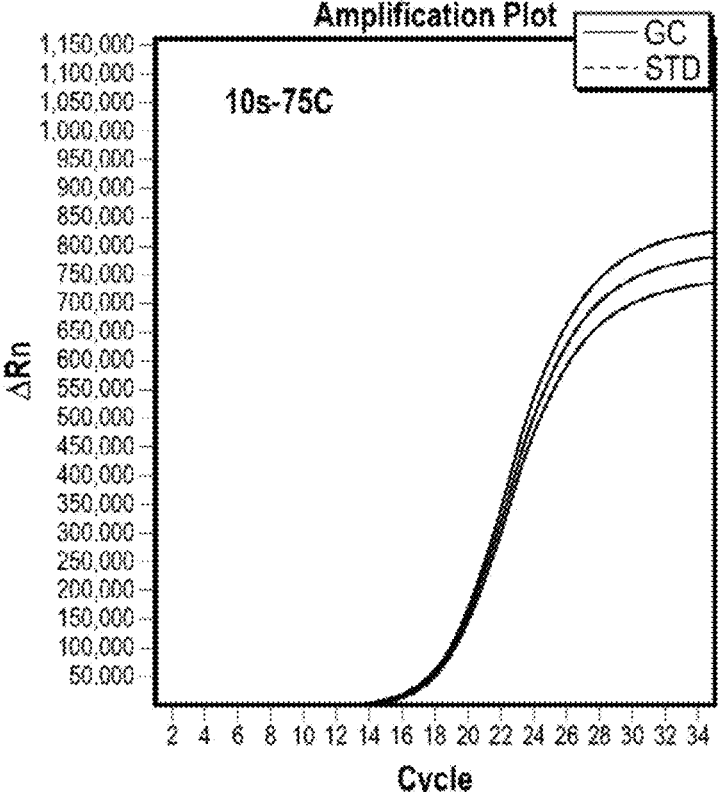
Figure 7:
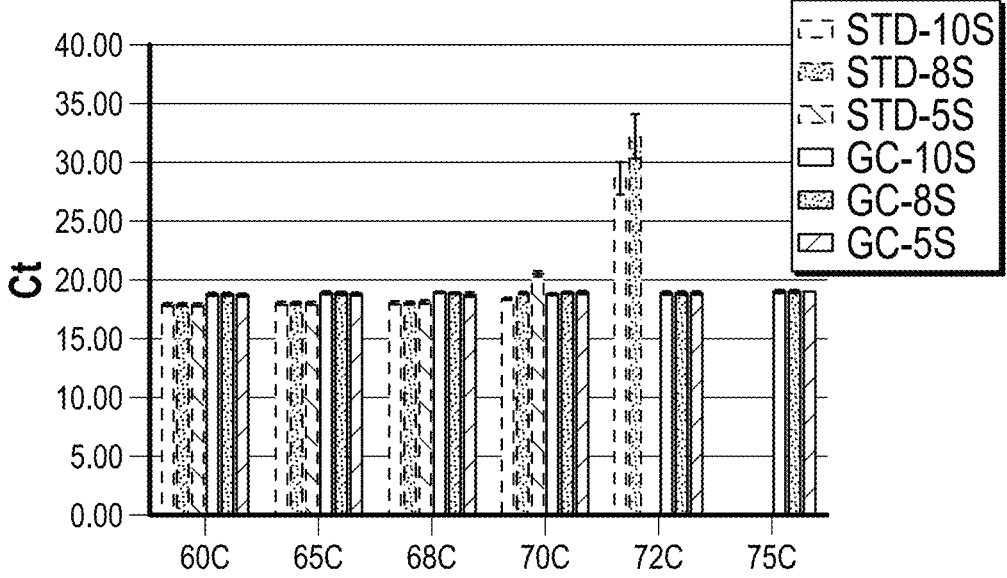
FIG. 7 contains an evaluation of Ct and dRn of PCR reactions using standard and GC-tailed primers across an annealing/amplification temperature gradient and at various duration times.
Figure 7:
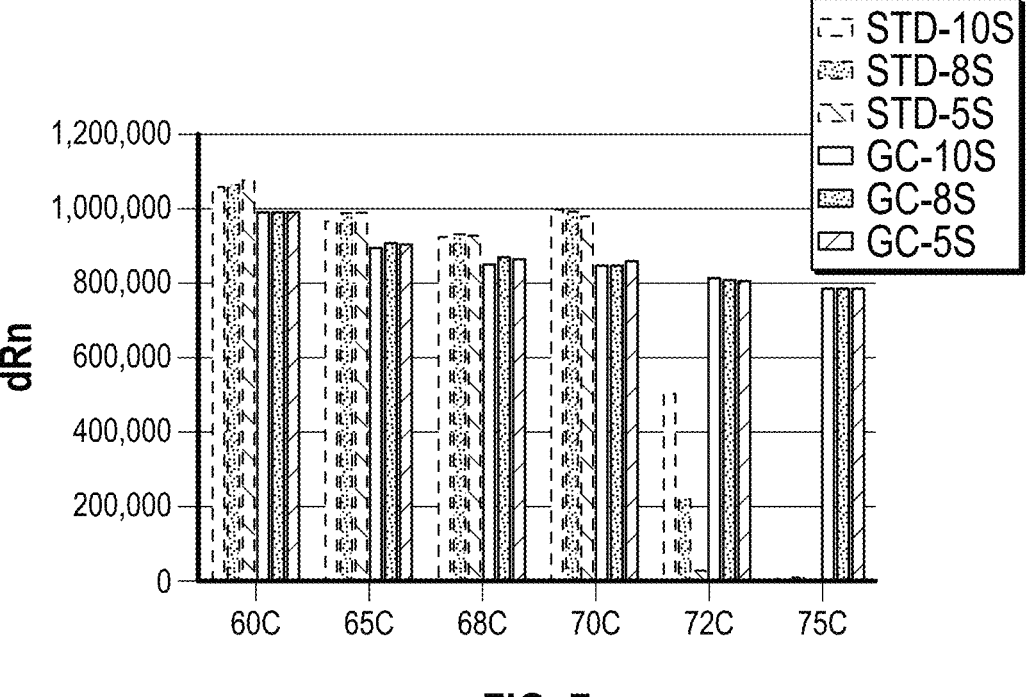

As can be seen in FIG. 6, GC-tailed primers were feasible at higher annealing temperatures and shorter durations. In contrast, standard primers were unable to amplify or had Ct delay when the extension temperature changed to 72° C. and 75° C. For example, as shown in FIG. 7, GC-tailed primers generated similar Ct values when using extension temperatures from 60° C.-75° C. In contrast, standard primers were unable to amplify or had Ct delay when the extension temperature changed to 72° C. and 75° C. When the extension temperature increased to 72° C.-75° C., the fluorescent signal slightly decreased in GC-tail primers, thus demonstrating a thermal influence on fluorescence that should be taken into account under certain circumstances.

Example 6: Optimization of Turnaround Time

In this Example, the turnaround times (TATs) of the various PCR profiles disclosed herein were compared to a standard, monolithic Fast PCR reaction.

The experimental setup was as follows. HBV hybrid gBlock template was utilized. Serial dilution $10^6$ copies/μl was tested. PCR was run in 10 μl total reaction volume and included the following: 1 μl sample, FTD MMX (5× buffer and 25×ENZ4), and 500 nM of the primers (103 bp standard primers and 113 bp GC-tailed primers HBV_FB_pm1_GC and HBV_FB_pm2_GC), and 100 nM of the probe HBV_FB_PR_FAM_BHQ+. The various PCR profiles utilized are shown in Table 7.

TABLE 7

| Step | Profile #1 | Profile #2 | Profile #3 | Profile #4 | Profile #5 (Standard) | Profile #6 |
|---|---|---|---|---|---|---|
| Hold* | 95° C./1 min | 95° C./1 min | 95° C./1 min | 95° C./1 min | 95° C./1 min | 95° C./1 min |
| Initiation phase | 5 cycles | 5 cycles | 5 cycles | 5 cycles | 40 cycles | 5 cycles |
| Denaturation* | 95° C./10 sec | 95° C./10 sec | 95° C./10 sec | 95° C./10 sec | 95° C./3 sec | 95° C./5 sec |
| Annealing/ Amplification* | 60° C./20 sec | 60° C./20 sec | 60° C./20 sec | 60° C./20 sec | 60° C./30 sec | 60° C./20 sec |

TABLE 7-continued

| Step | Profile #1 | Profile #2 | Profile #3 | Profile #4 | Profile #5 (Standard) | Profile #6 |
|---|---|---|---|---|---|---|
| Propagation phase | 35 cycles | 35 cycles | 34 cycles | 35 cycles | | 35 cycles |
| Denaturation* | 95° C./2 sec | 90° C./2 sec | 90° C./2 sec | 90° C./2 sec | | 90° C./2 sec |
| Annealing/ Amplification* | 60° C./10 sec | 72° C./10 sec | 72° C./10 sec | 72° C./10 sec | | 72° C./8 sec |
| | | | 1 cycle 90° C./2 sec 60° C./10 sec | 1 cycle 60° C./10 sec | | |
| Ramp rate | (4.82° C./s; 3.72° C./s) | (4.82° C./s; 3.72° C./s) | (4.82° C./s; 3.72° C./s) | (4.82° C./s; 3.72° C./s) | (4.82° C./s; 3.72° C./s) | (4.82° C./s; 3.72° C./s) |
| TAT | 21 min 26 sec | 16 min 44 sec | 16 min 49 sec | 16 min 57 sec | 33 min 56 sec | 15 min 9 sec |

*(Temp/time)

Figure 8:
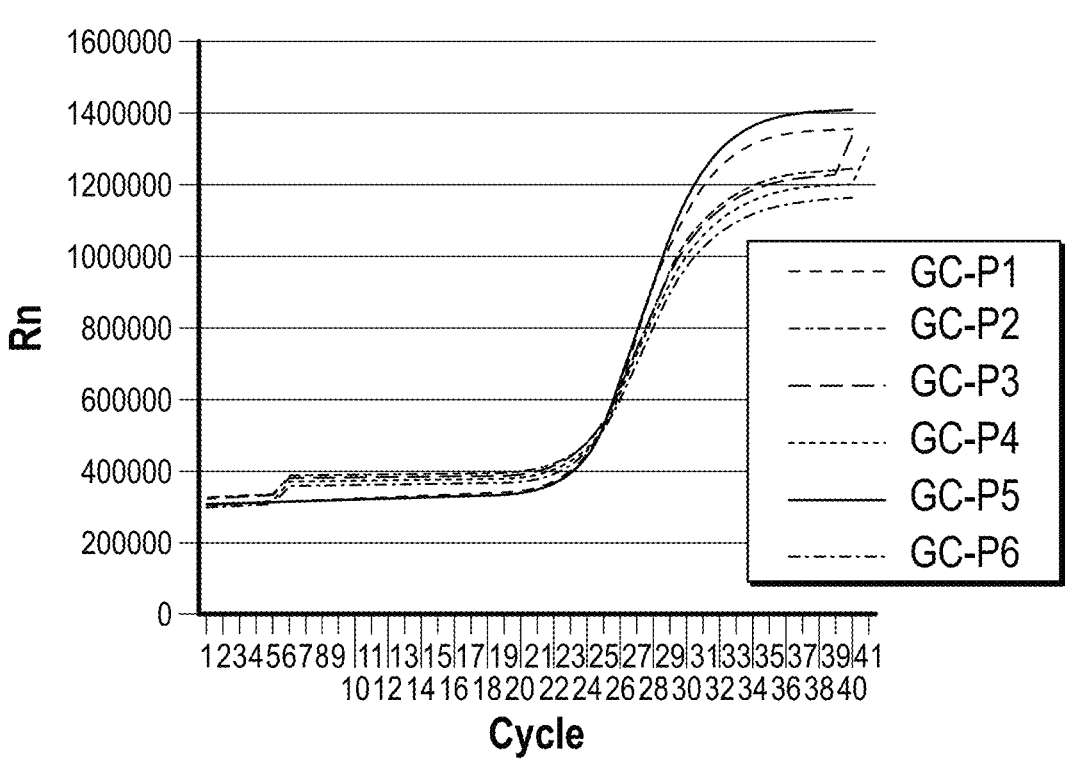
FIG. 8 contains amplification plots of PCR reactions using standard and GC-tailed primers at six different thermocycling profiles.
Figure 8:
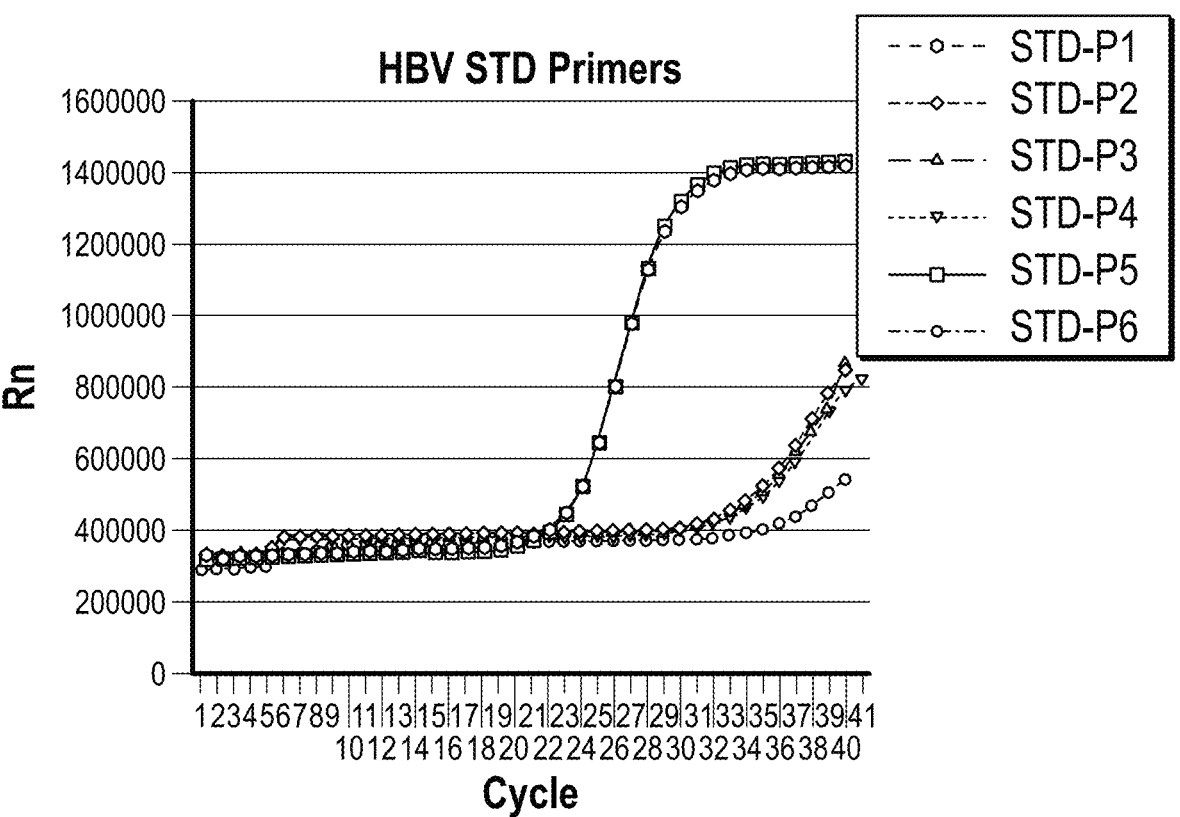
Figure 9:
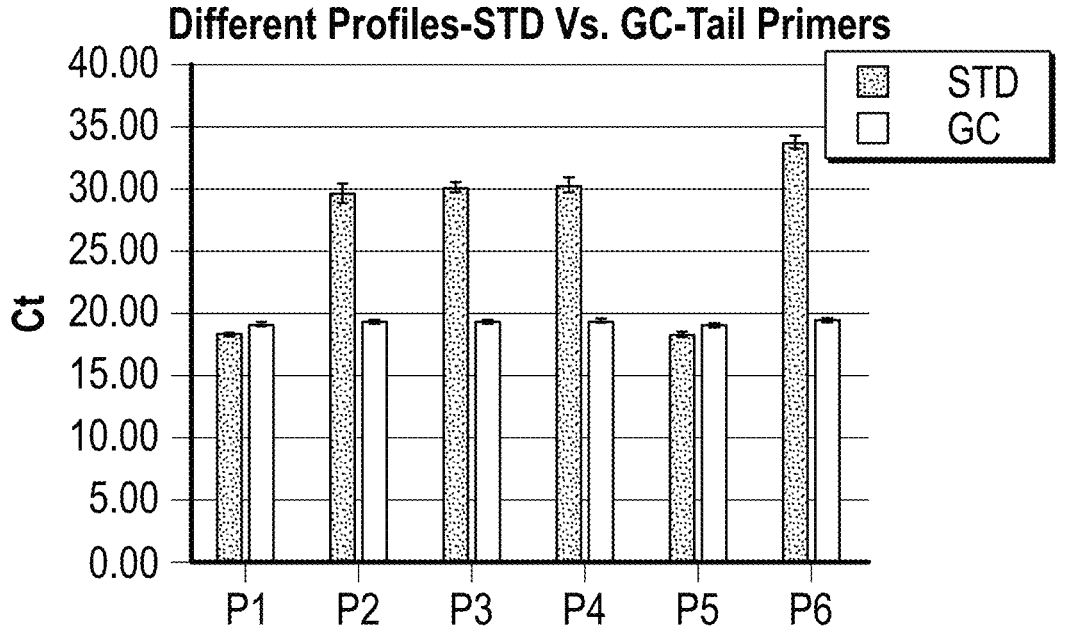
FIG. 9 contains an evaluation of Ct and dRn of PCR reactions using standard and GC-tailed primers at six different thermocycling profiles.
Figure 9:
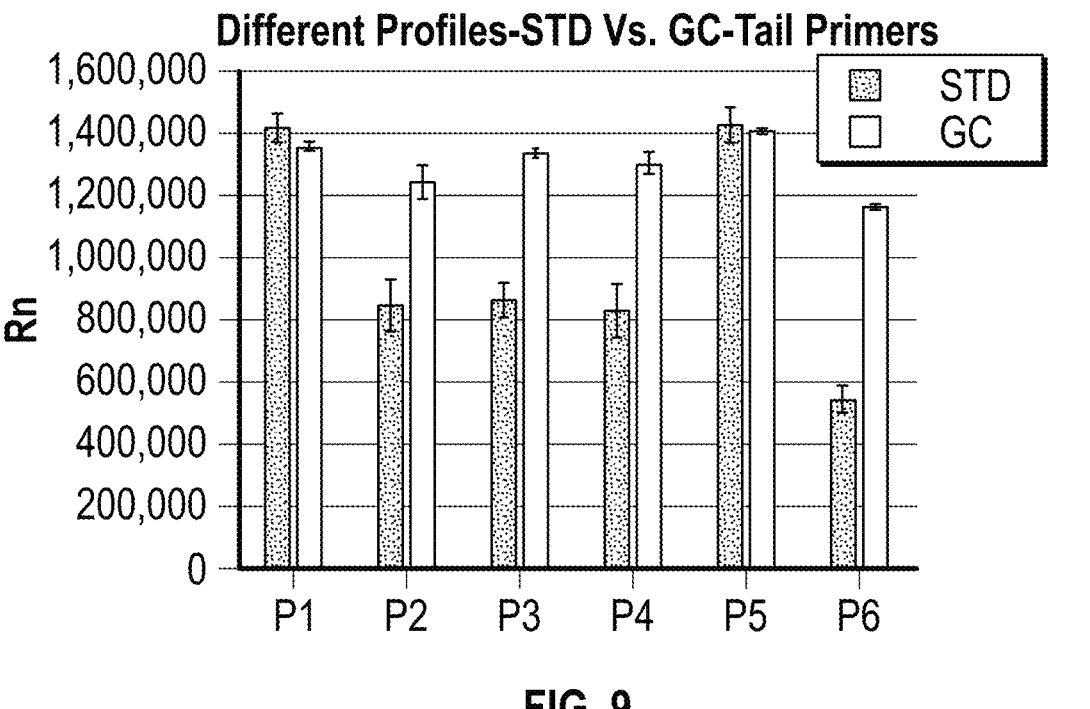

FIGS. 8-9 demonstrate the results obtained from the six different PCR profiles. The standard PCR profile was Profile 5; this profile included a single phase in which 40 identical cycles were performed. The standard PCR profile had a TAT of 33 minutes, 56 seconds. In contrast, Profiles 1~4 and 6 included two phases (initiation and propagation phases) that differed in both denaturation temperature and time as well as annealing/amplification temperature and time. The same initiation phase was used for each of Profiles 1~4 (i.e., 5 cycles of a denaturation step at 95° C. for 10 seconds followed by an annealing/amplification step at 60° C. for 20 seconds); Profile 6 was intended to be a "hot and fast" profile, and as such, had a similar initiation phase except that the time of the denaturation step was dropped to 5 seconds.

With respect to the propagation phases of Profiles 1-4, Profile #1 had the largest gap between denaturation and annealing/amplification temperatures; this 35° C. gap produced the highest TAT of 21 minutes, 26 seconds. When this gap between denaturation and annealing/amplification temperatures was reduced to 18° C., the TAT was reduced by almost five minutes (to 16 minutes, 44 seconds).

Profiles 3-4 were constructed to include a 60° C. final read step to evaluate the slight decrease in fluorescence signal in the GC-tailed primers; the data obtained from these two profiles demonstrated that the slight reduction in fluorescence is a pure temperature effect and thus solely due to a thermal interference.

Finally, Profile #6 was designed to demonstrate that it is possible to further reduce the TAT of the methods disclosed herein to 15 minutes by running a "hot and fast" reaction in which the time of the denaturation step in the initiation phase is cut in half and the annealing/amplification steps in the propagation phase are reduced from 10 seconds to 8 seconds.

Thus, in accordance with the present disclosure, there have been provided compositions and kits, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

25

26

The invention claimed is:

1. A method of amplifying a target nucleic acid in a biological sample, the method comprising the steps of:
  (i) adding to the biological sample a thermostable polymerase, nucleotides, and a pair of primers configured for amplification of the target nucleic acid to create an amplification mixture, wherein at least one of the primers comprises a hybridization stabilizer; and
  (ii) amplifying the target nucleic acid by polymerase chain reaction to produce an amplicon by thermally cycling the amplification mixture between at least a denaturation temperature and an elongation temperature through a plurality of amplification cycles, wherein the plurality of amplification cycles comprises at least one initiation cycle and at least one propagation cycle, and wherein a thermocycling profile of the initiation cycle is different from a thermocycling profile of the propagation cycle; and
  wherein the thermocycling profile of the at least one initiation cycle comprises a denaturation temperature in a range of from about 90° C. to about 100° C. that is held for about 2 to about 15 seconds, and an elongation temperature in a range of from about 55° C. to about 65° C. that is held for about 15 to about 30 seconds;
  wherein the thermocycling profile of the at least one propagation cycle comprises a denaturation temperature in a range of from about 80° C. to about 95° C. that is held for about 1 to about 5 seconds, and an elongation temperature in a range of from about 60° C. to about 75° C. that is held for about 1 to about 15 seconds, and wherein a difference between the elongation and denaturation temperatures in the at least one propagation cycle is 20° C. or less; and
  wherein the amplicon has a length in a range of from about 80 bp to about 300 bp, and wherein each primer has a length in a range of from about 21 to about 27 bp.

2. The method of claim 1, wherein the thermocycling profiles of the initiation and propagation cycles differ from one another in at least one of the denaturation temperature, a denaturation duration time, the elongation temperature, an elongation duration time, a ramp rate, and a cycle completion time.

3. The method of claim 1, wherein the amplicon has a full denaturation temperature in a range of from about 85° C. to about 95° C.

4. The method of claim 1, wherein the amplicon has a length of less than or equal to about 100 bp.

5. The method of claim 1, wherein the hybridization stabilizer comprises a tail at a 5' end of the primer, wherein the tail comprises a sequence that is non-complementary to the target nucleic acid.

6. The method of claim 1, wherein the hybridization stabilizer comprises a tail at a 5' end of the primer, wherein the tail consists of a sequence of G and/or C residues that is non-complementary to the target nucleic acid.

7. The method of claim 1, wherein the hybridization stabilizer comprises the presence of at least one modified nucleotide in the primer.

8. The method of claim 7, wherein the at least one modified nucleotide is C5-propynyl-dC (pdC) or C5-propynyl-dU (pdU).

9. The method of claim 7, wherein the at least one modified nucleotide is a locked nucleic acid (LNA).

10. The method of claim 1, wherein the plurality of amplification cycles also includes a single activation cycle prior to commencing the initiation cycle, wherein the activation cycle comprises a single hold step at a temperature of at least about 90° C. held for about 1 to about 5 minutes.

11. The method of claim 1, wherein the target nucleic acid is RNA, and wherein the method comprises exposing the biological sample to a reverse transcriptase to produce cDNA from the RNA target nucleic acid prior to performing step (ii).

12. The method of claim 1, wherein step (ii) includes about 3 to about 10 initiation cycles.

13. The method of claim 1, wherein step (ii) includes about 30 to about 45 propagation cycles.

14. The method of claim 1, wherein step (ii) is performed in less than about 20 minutes.

15. The method of claim 1, wherein step (ii) is performed in less than about 15 minutes.

16. A method of detecting a target nucleic acid in a biological sample, comprising the steps of:
  (i) adding to the biological sample a thermostable polymerase, nucleotides, and a pair of primers configured for amplification of the target nucleic acid to create an amplification mixture, wherein at least one of the primers comprises a hybridization stabilizer;
  (ii) amplifying the target nucleic acid by polymerase chain reaction to produce an amplicon by thermally cycling the amplification mixture between at least a denaturation temperature and an elongation temperature through a plurality of amplification cycles, wherein the plurality of amplification cycles comprises at least one initiation cycle and at least one propagation cycle, and wherein the thermocycling profile of the initiation cycle is different from the thermocycling profile of the propagation cycle; and
  (iii) detecting the presence of the amplified target nucleic acid using a probe; and
  wherein the thermocycling profile of the at least one initiation cycle comprises a denaturation temperature in a range of from about 90° C. to about 100° C. that is held for about 2 to about 15 seconds, and an elongation temperature in a range of from about 55° C. to about 65° C. that is held for about 15 to about 30 seconds;
  wherein the thermocycling profile of the at least one propagation cycle comprises a denaturation temperature in a range of from about 80° C. to about 95° C. that is held for about 1 to about 5 seconds, and an elongation temperature in a range of from about 60° C. to about 75° C. that is held for about 1 to about 15 seconds, and wherein a difference between the elongation and denaturation temperatures in the at least one propagation cycle vary from one another by about 20° C. or less; and
  wherein the amplicon has a length in a range of from about 80 bp to about 300 bp, and wherein each primer has a length in a range of from about 21 to about 27 bp.

17. The method of claim 16, wherein the probe comprises at least one modified nucleotide.

18. The method of claim 17, wherein the at least one modified nucleotide is C5-propynyl-dC (pdC) or C5-propynyl-dU (pdU).

19. The method of claim 17, wherein the at least one modified nucleotide is a locked nucleic acid (LNA).

20. The method of claim 16, wherein the probe comprises at least one minor groove binder (MGB) moiety at a 3' end thereof.

21. A method of amplifying a target nucleic acid in a biological sample, the method comprising the steps of:
  (i) adding to the biological sample a thermostable polymerase, nucleotides, and a pair of primers configured for amplification of the target nucleic acid to create an amplification mixture, wherein at least one of the primers comprises a hybridization stabilizer, wherein the hybridization stabilizer is selected from the group consisting of:

(a) a tail at a 5' end of the primer, and wherein the tail consists of a sequence of G and/or C residues that is non-complementary to the target nucleic acid; and/or (b) at least one modified nucleotide in the primer, wherein the at least one modified nucleotide is selected from the group consisting of C5-propynyl-dC (pdC), C5-propynyl-dU (pdU), a locked nucleic acid (LNA), and combinations thereof;

(ii) amplifying the target nucleic acid by polymerase chain reaction to produce an amplicon by thermally cycling the amplification mixture between at least a denaturation temperature and an elongation temperature through a plurality of amplification cycles, wherein the plurality of amplification cycles comprises at least one initiation cycle and at least one propagation cycle, and wherein a thermocycling profile of the initiation cycle is different from a thermocycling profile of the propagation cycle, and wherein a difference between the elongation and denaturation temperatures of the propagation cycle is 20° C. or less; and wherein the amplicon has a length in a range of from about 80 bp to about 300 bp, and wherein each primer has a length in a range of from about 21 to about 27 bp.

22. The method of claim 21, further comprising the step of:

(iii) detecting the presence of the amplified target nucleic acid using a probe.

23. The method of claim 21, wherein the thermocycling profiles of the initiation and propagation cycles differ from one another in at least one of the denaturation temperature, a denaturation duration time, the elongation temperature, an elongation duration time, a ramp rate, and a cycle completion time.

24. The method of claim 21, wherein the amplicon has a full denaturation temperature in a range of from about 85° C. to about 95° C.

25. The method of claim 21, wherein the plurality of amplification cycles also includes a single activation cycle prior to commencing the initiation cycle, wherein the activation cycle comprises a single hold step at a temperature of at least about 90° C. held for about 1 to about 5 minutes.

26. The method of claim 21, wherein the target nucleic acid is RNA, and wherein the method comprises exposing the biological sample to a reverse transcriptase to produce cDNA from the RNA target nucleic acid prior to performing step (ii).

27. The method of claim 21, wherein the thermocycling profile of the at least one initiation cycle comprises a denaturation temperature in a range of from about 90° C. to about 100° C. that is held for about 2 to about 15 seconds, and an elongation temperature in a range of from about 55° C. to about 65° C. that is held for about 15 to about 30 seconds.

28. The method of claim 27, wherein step (ii) includes about 3 to about 10 initiation cycles.

29. The method of claim 21, wherein the thermocycling profile of the at least one propagation cycle comprises a denaturation temperature in a range of from about 80° C. to about 95° C. that is held for about 1 to about 5 seconds, and an elongation temperature in a range of from about 60° C. to about 75° C. that is held for about 1 to about 15 seconds.

30. The method of claim 29, wherein step (ii) includes about 30 to about 45 propagation cycles.

31. The method of claim 21, wherein step (ii) is performed in less than about 20 minutes.

32. The method of claim 21, wherein step (ii) is performed in less than about 15 minutes.

* * * * *

SEQUENCE LISTING

```
<160> NUMBER OF SEQ ID NOS: 8

<210> SEQ ID NO 1
<211> LENGTH: 31
<212> TYPE: DNA
<213> ORGANISM: Artificial sequence
<220> FEATURE:
<223> OTHER INFORMATION: Primer sequence with 5' GC-rich tail

<400> SEQUENCE: 1
gcgcctggat gtgtctgcgg cgtttttatca t                              31

<210> SEQ ID NO 2
<211> LENGTH: 26
<212> TYPE: DNA
<213> ORGANISM: Artificial Sequence
<220> FEATURE:
<223> OTHER INFORMATION: Primer sequence with 5' GC-rich tail

<400> SEQUENCE: 2
ggcgggacaa acgggcaaca tacctt                                     26

<210> SEQ ID NO 3
<211> LENGTH: 23
```

```
<212> TYPE: DNA
<213> ORGANISM: Artificial Sequence
<220> FEATURE:
<223> OTHER INFORMATION: Primer sequence with pdU and pdC residues

<400> SEQUENCE: 3
atcctgctgc tatgcctcat ctt                                              23

<210> SEQ ID NO 4
<211> LENGTH: 201
<212> TYPE: DNA
<213> ORGANISM: Hepatitis B virus

<400> SEQUENCE: 4
ctcacaatac cgcagagtct agactcgtgg tggacttctc tcaattttct aggggggaact    60 accgtgtgtc ttggccaaaa ttcgcagtcc ccaacctcca atcactcacc aacctcttgt    120
cctccaactt gtcctggtta tcgctggatg tgtctgcggc gttttatcat cttcctcttc    180
atcctgctgc tatgcctcat c                                              201

<210> SEQ ID NO 5
<211> LENGTH: 113
<212> TYPE: DNA
<213> ORGANISM: Artificial sequence
<220> FEATURE:
<223> OTHER INFORMATION: Hepatitis B virus amplicon with GC-rich tails
      on either end

<400> SEQUENCE: 5
gcgcctggat gtgtctgcgg cgttttatca tcttcctctt catcctgctg ctatgcctca    60
tcttcttgtt ggttcttctg gactatcaag gtatgttgcc cgtttgtccc gcc           113

<210> SEQ ID NO 6
<211> LENGTH: 27
<212> TYPE: DNA
<213> ORGANISM: Artificial sequence
<220> FEATURE:
<223> OTHER INFORMATION: Primer sequence with 5' GC-rich tail

<400> SEQUENCE: 6
ggcgagactc gtggtggact tctctca                                         27

<210> SEQ ID NO 7
<211> LENGTH: 24
<212> TYPE: DNA
<213> ORGANISM: Artificial sequence
<220> FEATURE:
<223> OTHER INFORMATION: Primer sequence with 5' GC-rich tail

<400> SEQUENCE: 7
ggcggcatag cagcaggatg caga                                            24

<210> SEQ ID NO 8
<211> LENGTH: 27
<212> TYPE: DNA
<213> ORGANISM: Artificial sequence
<220> FEATURE:
<223> OTHER INFORMATION: Primer sequence with pdU and pdC residues

<400> SEQUENCE: 8
tctgcggcgt tttatcatct tcctctt                                         27
```